United States Patent
Ramadas et al.

(10) Patent No.: US 11,854,553 B2
(45) Date of Patent: Dec. 26, 2023

(54) CYBERSECURITY FOR SENSITIVE-INFORMATION UTTERANCES IN INTERACTIVE VOICE SESSIONS

(71) Applicant: Optum Technology, Inc., Eden Prairie, MN (US)

(72) Inventors: Devikiran Ramadas, Bangalore (IN); Gregory J Boss, Saginaw, MI (US); Ninad Sathaye, Bangalore (IN); Raghav Bali, Bangalore (IN); Nitin Dwivedi, Bangalore (IN)

(73) Assignee: OPTUM TECHNOLOGY, INC., Eden Prairie, MN (US)

( * ) Notice: Subject to any disclaimer, the term of this patent is extended or adjusted under 35 U.S.C. 154(b) by 0 days.

(21) Appl. No.: 17/133,311

(22) Filed: Dec. 23, 2020

(65) Prior Publication Data

US 2022/0199093 A1   Jun. 23, 2022

(51) Int. Cl.
*G10L 17/14*   (2013.01)
*G10L 17/24*   (2013.01)
(Continued)

(52) U.S. Cl.
CPC .............. *G10L 17/14* (2013.01); *G10L 15/22* (2013.01); *G10L 17/24* (2013.01); *G10L 25/18* (2013.01); *G10L 2015/225* (2013.01)

(58) Field of Classification Search
CPC ......... G10L 17/14; G10L 15/22; G10L 17/24; G10L 25/18; G10L 2015/225
See application file for complete search history.

(56) References Cited

U.S. PATENT DOCUMENTS

| | | |
|---|---|---|
| 7,502,741 B2 | 3/2009 | Finke et al. |
| 8,244,531 B2 | 8/2012 | Erhart et al. |
| | (Continued) | |

FOREIGN PATENT DOCUMENTS

| | | |
|---|---|---|
| EP | 2924966 B1 | 4/2020 |
| EP | 3386165 B1 | 9/2021 |
| | (Continued) | |

OTHER PUBLICATIONS

Claburn, "Is it possible to control Amazon Alexa, Google Now using inaudible commands? Absolutely", The Register, Retrieved Apr. 13, 2021 from: https://www.theregister.com/2017/08/25/amazon_alexa_answers_inaudible_commands/, Aug. 25, 2017, 2 pp.

(Continued)

*Primary Examiner* — Daniel C Washburn
*Assistant Examiner* — James Boggs
(74) *Attorney, Agent, or Firm* — Shumaker & Sieffert, P.A.

(57) ABSTRACT

A method comprises obtaining, by a computing system, first audio data representing one or more initial utterances during an interactive voice session with an interactive voice system; generating, by the computing system, based on the first audio data, a prediction regarding whether a subsequent utterance of a user during the interactive voice session will contain sensitive information, the subsequent utterance following the one or more initial utterances in time; obtaining, by the computing system, second audio data representing the subsequent utterance; determining, by the computing system, based on the prediction, whether to transmit the second audio data; and based on a determination not to transmit the second audio data: replacing, by the computing system, the second audio data with third audio data that is based on a voice of the user; and transmitting, by the computing system, the third audio data.

15 Claims, 11 Drawing Sheets

(51) Int. Cl.
    *G10L 25/18*     (2013.01)
    *G10L 15/22*     (2006.01)

(56) References Cited

U.S. PATENT DOCUMENTS

| | | | |
|---|---|---|---|
| 8,433,915 B2 | 4/2013 | Doren | |
| 8,572,758 B1 | 10/2013 | Clifford | |
| 9,697,837 B2 | 7/2017 | Hefetz | |
| 9,787,835 B1 * | 10/2017 | Pycko | H04M 3/56 |
| 10,032,066 B2 | 7/2018 | Gongaware et al. | |
| 10,237,730 B2 | 3/2019 | Benoit et al. | |
| 10,326,798 B2 | 6/2019 | Lambert | |
| 10,402,826 B2 | 9/2019 | Tew et al. | |
| 10,530,571 B2 | 1/2020 | Moon et al. | |
| 10,540,521 B2 * | 1/2020 | Baracaldo Angel | G10L 21/0208 |
| 10,728,384 B1 * | 7/2020 | Channakeshava | G06F 21/6245 |
| 10,885,902 B1 * | 1/2021 | Papania-Davis | G10L 15/1815 |
| 11,024,295 B2 * | 6/2021 | Schmidt | G10L 15/22 |
| 11,039,013 B1 | 6/2021 | Garrod et al. | |
| 11,138,334 B1 * | 10/2021 | Garrod | G10L 15/02 |
| 11,210,461 B2 * | 12/2021 | Thomson | G10L 15/22 |
| 11,217,223 B2 * | 1/2022 | Gkoulalas-Divanis | G10L 21/00 |
| 11,482,220 B1 * | 10/2022 | Kosowski | G10L 15/22 |
| 2003/0105634 A1 | 6/2003 | Abella et al. | |
| 2005/0005145 A1 | 1/2005 | Teixeira | |
| 2010/0082342 A1 | 4/2010 | Erhart et al. | |
| 2012/0027195 A1 | 2/2012 | Shaffer et al. | |
| 2015/0215112 A1 | 7/2015 | Moon | |
| 2018/0091487 A1 | 3/2018 | Lin et al. | |
| 2018/0137295 A1 | 5/2018 | Sharma | |
| 2019/0057698 A1 | 2/2019 | Raanani et al. | |
| 2019/0158889 A1 | 5/2019 | Xue | |
| 2020/0196141 A1 * | 6/2020 | Baker | H04R 3/00 |
| 2020/0314133 A1 | 10/2020 | Singh et al. | |
| 2021/0389924 A1 * | 12/2021 | Chong | H04W 12/02 |
| 2022/0019671 A1 | 1/2022 | Boone et al. | |
| 2022/0084501 A1 | 3/2022 | Ananthapur Bache et al. | |
| 2022/0092583 A1 | 3/2022 | Ur et al. | |
| 2022/0114274 A1 | 4/2022 | Fathalla et al. | |
| 2022/0199073 A1 | 6/2022 | Ramadas et al. | |
| 2022/0270599 A1 | 8/2022 | Nitzberg et al. | |
| 2022/0303502 A1 | 9/2022 | Fisher et al. | |

FOREIGN PATENT DOCUMENTS

| | | |
|---|---|---|
| GB | 2578121 A | 4/2020 |
| WO | 2012170128 A1 | 12/2012 |
| WO | 2019110574 A1 | 6/2019 |

OTHER PUBLICATIONS

Vincent, "Inaudible ultrasound commands can be used to secretly control Siri, Alexa, and Google Now", TheVerge, Retrieved Apr. 13, 2021 from: https://www.theverge.com/2017/9/7/16265906/ultrasound-hack-siri-alexa-google, Sep. 7, 2017, 4 pp.
Cohn et al., "Audio De-identification: A New Entity Recognition Task," ArXiv.org, arXiv: 1903.07037, May 5, 2019, 8 pp.
Jia et al., "Direct speech-to-speech translation with a sequence-to-sequence model," ArXiv.org, arXiv: 1904.06037, Jun. 25, 2019, 5 pp.
Kemler, "If it has audio, now it can have captions," Google, Retrieved Apr. 19, 2021 from: https://www.blog.google/products/android/live-caption/, Oct. 16, 2019, 4 pp.
SiriTeam, "Hey Siri: An On-device DNN-powered Voice Trigger for Apple's Personal Assistant," Apple, Inc., Retrieved Apr. 19, 2021 from: https://machinelearning.apple.com/research/hey-siri, Oct. 2017, 11 pp.
Perez, "Amazon Alexa launches its first HIPAA-compliant medical skills," Verizon Media; TechCrunch, Retrieved Aug. 31, 2020 from: https://techcrunch.com/2019/04/04/amazon-alexa-launches-its-first-hipaa-compliant-medical-skills/, Apr. 4, 2019, 12 pp.
Day et al., "Amazon's Alexa Team Can Access Users' Home Addresses," Bloomberg Technology, Retrieved Apr. 22, 2021 from: https://web.archive.org/web/20200725032323/https://www.bloomberg.com/news/articles/2019-04-24/amazon-s-alexa-reviewers-can-access-customers-home-addresses, Apr. 24, 2019, 4 pp.
Day et al., "Amazon Workers Are Listening to What You Tell Alexa," Bloomberg Technology, Retrieved Apr. 22, 2021 from: https://web.archive.org/web/20200725032141/https://www.bloomberg.com/news/articles/2019-04-10/is-anyone-listening-to-you-on-alexa-a-global-team-reviews-audio, Apr. 10, 2019, 7 pp.
McCoy, "Target to pay $18.5M for 2013 data breach that affected 41 million consumers," USA Today, Retrieved Apr. 22, 2021 from: https://web.archive.org/web/20200813213810if_/https://www.usatoday.com/story/money/2017/05/23/target-pay-185m-2013-data-breach-affected-consumers/102063932/, May 23, 2017, 2 pp.
U.S. Appl. No. 17/133,334, filed Dec. 23, 2020, naming inventors Ramadas et al.
Gandhi et al., "A Study on Current Scenario of Audio Encryption", International Journal of Computer Applications, vol. 116, No. 7, Apr. 2015, pp. 13-17.
Krasnowski et al., "Introducing a Verified Authenticated Key Exchange Protocol over Voice Channels for Secure Voice Communication", ICISSP, 2020, pp. 683-690, (Applicant points out, in accordance with MPEP 609.04(a), that the year of publication, 2020, is sufficiently earlier than the effective U.S. filing date, so that the particular month of publication is not in issue.).
U.S. Appl. No. 17/652,057, filed Feb. 22, 2022, naming inventors Ramadas et al.
Prosecution History from U.S. Appl. No. 17/652,057, dated Oct. 6, 2022 through Jan. 6, 2023, 25 pp.
Final Office Action from U.S. Appl. No. 17/652,057 dated Jul. 6, 2023, 13 pp.
Response to Final Office Action dated Jul. 6, 2023 from U.S. Appl. No. 17/652,057, filed Oct. 6, 2023, 14 pp.

* cited by examiner

CYBERSECURITY FOR SENSITIVE-INFORMATION UTTERANCES IN INTERACTIVE VOICE SESSIONS

BACKGROUND

As voice recognition technology has matured, it has become easier for individuals to interact with organizations through interactive voice systems, such as voice assistant systems. Examples of voice assistant systems include ALEXA™ from Amazon.com, Inc., SIRI™ from Apple Inc., Google Assistant from Alphabet Inc., CORTANA™ from Microsoft Corporation, and so on. Such interactive voice systems may serve as channels through which an organization can receive information from a user. For example, a healthcare provider may receive information from a user indicating that the user wants to schedule an appointment.

An interactive voice session is a session with an interactive voice system. During an interactive voice session, the user may provide sensitive information. For example, the user may provide their Social Security number (SSN), personally identifiable information, information about health conditions, bank account numbers, home address, telephone number, or other types of sensitive information. Sensitive information of this type may be the target for malicious actors. For instance, malicious actors may use sensitive information of this type for purposes of identity theft, extortion, doxing, social engineering, and other malign activities.

SUMMARY

The present disclosure describes devices, systems, and methods for protecting sensitive information in spoken content during interactive voice sessions. As described herein, a computing system may predict an occurrence and duration of a sensitive-information utterance during an interactive voice session. The sensitive-information utterance is a spoken utterance of a user in which the user utters potentially sensitive information. The computing system may de-identify the sensitive-information utterance or otherwise prevent transmission of the sensitive-information utterance during the interactive voice session. For instance, the computing system may mask the sensitive-information utterance so that sensitive information in the sensitive-information utterance is obfuscated. In some examples, the computing system may obfuscate the sensitive-information utterance by replacing the sensitive-information utterance with alternative audio data based on a voice of the user. In some examples, obfuscating the sensitive-information utterance may prevent a party receiving other information through the interactive voice session from obtaining the sensitive information utterance. In some examples, obfuscating the sensitive information may prevent the sensitive-information utterance from being obtained by a third-party interactive voice system that facilitates the interactive voice session. Obfuscating the sensitive information utterance may also prevent third parties from intercepting the sensitive-information utterance. In some examples, the computing system may prevent transmission of a sensitive-information utterance based on a risk profile of a channel through which the interactive voice session is conducted. In this way, the techniques of this disclosure may provide cybersecurity enhancements for computing systems.

In one example, this disclosure describes a method comprising: obtaining, by a computing system, first audio data representing one or more initial utterances during an interactive voice session with an interactive voice system; generating, by the computing system, based on the first audio data, a prediction regarding whether a subsequent utterance of a user during the interactive voice session will contain sensitive information, the subsequent utterance following the one or more initial utterances in time; obtaining, by the computing system, second audio data representing the subsequent utterance; determining, by the computing system, based on the prediction, whether to transmit the second audio data; and based on a determination not to transmit the second audio data: replacing, by the computing system, the second audio data with third audio data that is based on a voice of the user; and transmitting, by the computing system, the third audio data.

In another example, this disclosure describes a computing system comprising: one or more storage devices configured to store first audio data representing one or more initial utterances during an interactive voice session with an interactive voice system; and processing circuitry configured to: generate, based on the first audio data, a prediction regarding whether a subsequent utterance of a user during the interactive voice session will contain sensitive information, the subsequent utterance following the one or more initial utterances in time; and obtain second audio data representing the subsequent utterance; determine, based on the prediction, whether to transmit the second audio data; and based on a determination not to transmit the second audio data: replace the second audio data with third audio data that is based on a voice of the user; and transmit the third audio data.

In another example, this disclosure describes a computer-readable storage medium comprising instructions that, when executed, cause processing circuitry of a computing system to: obtain first audio data representing one or more initial utterances during an interactive voice session with an interactive voice system; generate, based on the first audio data, a prediction regarding whether a subsequent utterance of a user during the interactive voice session will contain sensitive information, the subsequent utterance following the one or more initial utterances in time; and obtain second audio data representing the subsequent utterance; determine, based on the prediction, whether to transmit the second audio data; and based on a determination not to transmit the second audio data: replace the second audio data with third audio data that is based on a voice of the user; and transmit the third audio data.

In one example, this disclosure describes a method that includes obtaining, by a computing system, first audio data representing one or more initial utterances during an interactive voice session with an interactive voice system; generating, by the computing system, based on the first audio data, a prediction regarding whether a subsequent utterance of a user in the interactive voice session will contain sensitive information, wherein the subsequent utterance follows the one or more initial utterances in time; obtaining, by the computing system, second audio data representing the subsequent utterance; determining, by the computing system, based on the prediction and based on a risk profile of the interactive voice system, whether to transmit the second audio data to the interactive voice system; and based on the determination to transmit the second audio data to the interactive voice system, transmitting the second audio data to the interactive voice system.

In another example, this disclosure describes a computing system that includes a memory configured to store first audio data representing one or more initial utterances during an interactive voice session with an interactive voice system; and processing circuitry configured to: generate, based on the first audio data, a prediction regarding whether a subsequent utterance of a user in the interactive voice session will contain sensitive information, wherein the subsequent utterance follows the one or more initial utterances in time; obtain second audio data representing the subsequent utterance; determine, based on the prediction and based on a risk profile of the interactive voice system, whether to transmit the second audio data to the interactive voice system; and based on the determination to transmit the second audio data to the interactive voice system, transmit the second audio data to the interactive voice system.

In another example, this disclosure describes a computer-readable storage medium that includes obtain first audio data representing one or more initial utterances during an interactive voice session with an interactive voice system; generate, based on the first audio data, a prediction regarding whether a subsequent utterance of a user in the interactive voice session will contain sensitive information, wherein the subsequent utterance follows the one or more initial utterances in time; obtain, by the computing system, second audio data representing the subsequent utterance; determine, based on the prediction and based on a risk profile of the interactive voice system, whether to transmit the second audio data to the interactive voice system; and based on the determination to transmit the second audio data to the interactive voice system, transmit the second audio data to the interactive voice system.

The details of one or more aspects of the disclosure are set forth in the accompanying drawings and the description below. Other features, objects, and advantages of the techniques described in this disclosure will be apparent from the description, drawings, and claims.

DETAILED DESCRIPTION

Figure 1:
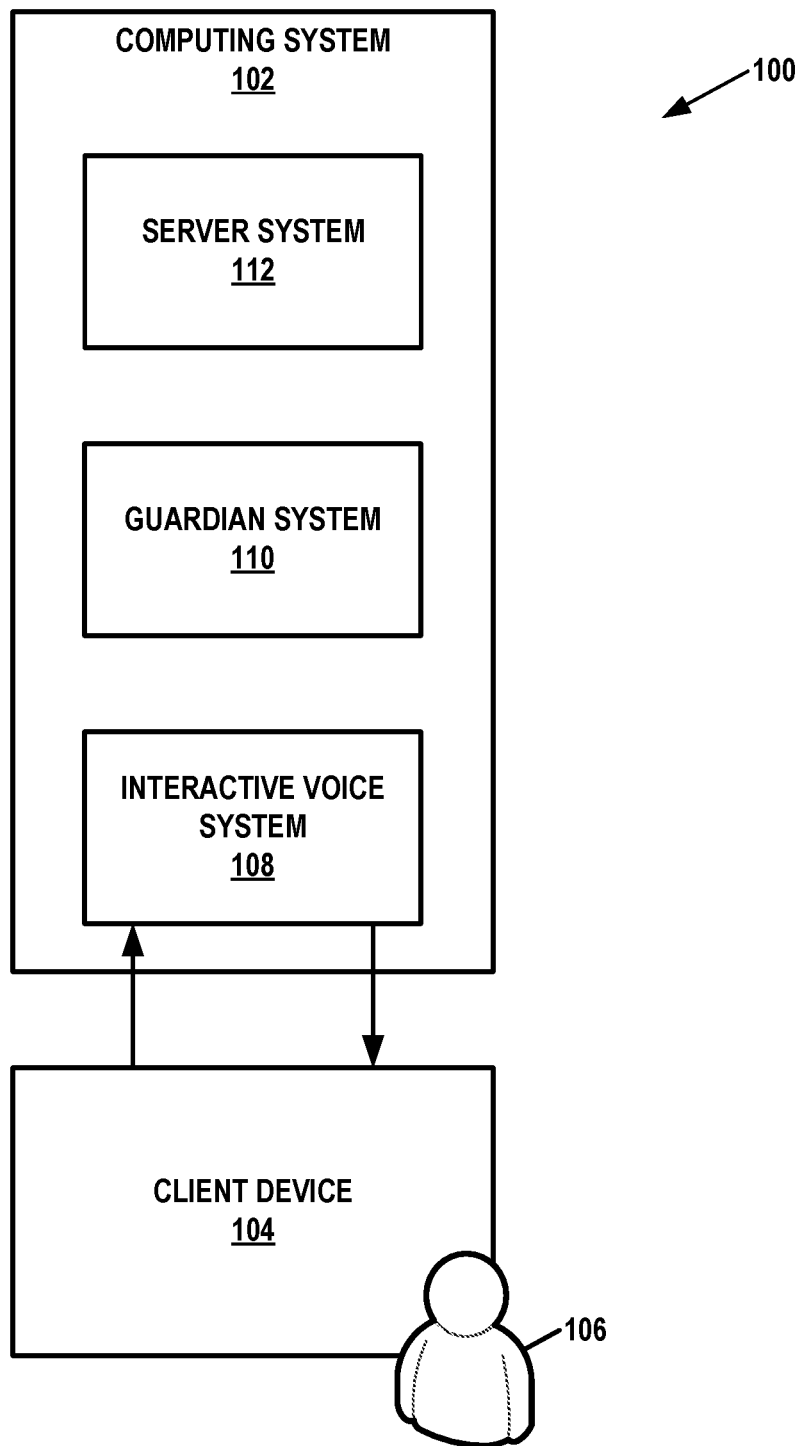
FIG. 1 is a block diagram illustrating an example system in accordance with one or more aspects of this disclosure.

FIG. 1 is a block diagram illustrating an example system 100 in accordance with one or more aspects of this disclosure. In the example of FIG. 1, system 100 includes a computing system 102 and a client device 104. In other examples, system 100 may include more, fewer, or different components.

Computing system 102 may include one or more computing devices. In examples where computing system 102 includes two or more computing devices, the computing devices of computing system 102 may act together as a system. Example types of computing devices include server devices, personal computers, handheld computers, intermediate network devices, data storage devices, and so on. In examples where computing system 102 includes two or more computing devices, the computing devices of computing system 102 may be geographically distributed or concentrated together (e.g., in a single data center). Moreover, different organizations may operate different computing devices within computing system 102.

Client device 104 is configured to generate audio data representing sounds generated by a user 106. Client device 104 may also be configured to generate sound based on audio data generated by computing system 102 or another source. Client device 104 may also include one or more devices. For example, client device 104 may include a smart speaker device, a personal computer, a mobile phone, a tablet computer, an ambient computing device, an Internet of Things (IoT) device, or another type of device. Computing system 102 and client device 104 may be configured to communicate via one or more communication networks, such as the Internet. In some examples, client device 104 is included in the one or more computing devices of computing system 102.

In the example of FIG. 1, computing system 102 is configured to implement an interactive voice system (IVS) 108, a guardian system 110, and a server system 112. IVS 108 may be configured to obtain audio data from client device 104 and process the audio data to determine semantic content of the audio data. In other words, IVS 108 may determine what speech sounds represented by the audio data mean. Additionally, IVS 108 may send response audio data to client device 104. The response audio data may represent sound that may, e.g., be responsive to the semantic content of the audio data obtained from client device 104. In some examples, IVS 108 may be or may include a voice assistant system, such as ALEXA by Amazon.com Inc., SIRI by Apple Inc., CORTANA by Microsoft Corp., or another type of voice assistant system. In some examples, IVS 108 may be implemented at least in part as an application on client device 104. In some examples, IVS 108 is implemented as part of a web application. In some examples, IVS 108 may include a voice user interface system. Although depicted in the example of FIG. 1 as being part of computing system 102, some or all of the functionality of IVS 108 may be implemented in client device 104 or another device. For instance, some of the functionality of IVS 108 may be implemented in client device 104 and some of the functionality of IVS 108 may be implemented in computing system 102.

User 106 may engage in an interactive voice session with IVS 108. During an interactive voice session with IVS 108, user 106 may utter various types of statements to client device 104. Example types of statements may include requests, responses to questions, formalities, commands, and so on. For example, user 106 may utter a spoken request to client device 104 to request a visit to a healthcare provider. In another example, user 106 may utter a spoken request to client device 104 to access financial information. Client device 104 may obtain response audio data from IVS 108 and output sound, such as utterances, based on the response audio data. For instance, user 106 may say "I'd like to schedule an appointment with a dermatologist" and client device 104 may say "I can help you with that" based on response audio data generated by IVS 108. In some examples where client device 104 includes a display screen, client device 104 may receive data from computing system 102 (e.g., from IVS 108) and may display the data on the display screen.

In some examples, IVS 108 provides semantic data to server system 112. For example, if the audio data obtained by IVS 108 represents speech indicating a request to visit a physical therapist, IVS 108 may provide semantic data to server system 112 indicating that user 106 wants to visit a physical therapist. In some examples, IVS 108 may provide some or all of the audio data to server system 112. In some examples where IVS 108 provides some or all of the audio data to server system 112, server system 112 may determine semantic data of the utterances based on the audio data. In some examples, specific functionality of server system 112 may be a "skill" of a voice assistant system.

Server system 112 may process the semantic data in various ways. For example, server system 112 may store the semantic data, use the semantic data in an Application Programming Interface (API) to perform specific functions, and so on. Furthermore, in some examples, based on the semantic data, server system 112 may generate response data. In some examples, IVS 108 may use the response data to synthesize response audio data representing a spoken version of the response data. IVS 108 may provide the response audio data to client device 104. In some examples, the response data generated by server system 112 includes audio data and IVS 108 may forward the audio data to client device 104. Client device 104 may output sound based on the received audio data.

Guardian system 110 may be configured to intercept sensitive-information utterances during interactive voice sessions. In some examples, guardian system 110 may obfuscate the intercepted sensitive-information utterances. In some examples, guardian system 110 may determine whether to transmit the sensitive-information utterances via IVS 108. As part of intercepting sensitive-information utterances, guardian system 110 may predict that user 106 is about to speak a sensitive-information utterance and may predict a temporal duration of the sensitive-information utterance. For example, guardian system 110 may determine that user 106 has said, "my social security number is" or that client device 104 has output an utterance that said, "what is your social security number?". In this example, guardian system 110 may therefore determine that the next utterance of user 106 will be the social security number of user 106.

Figure 2:
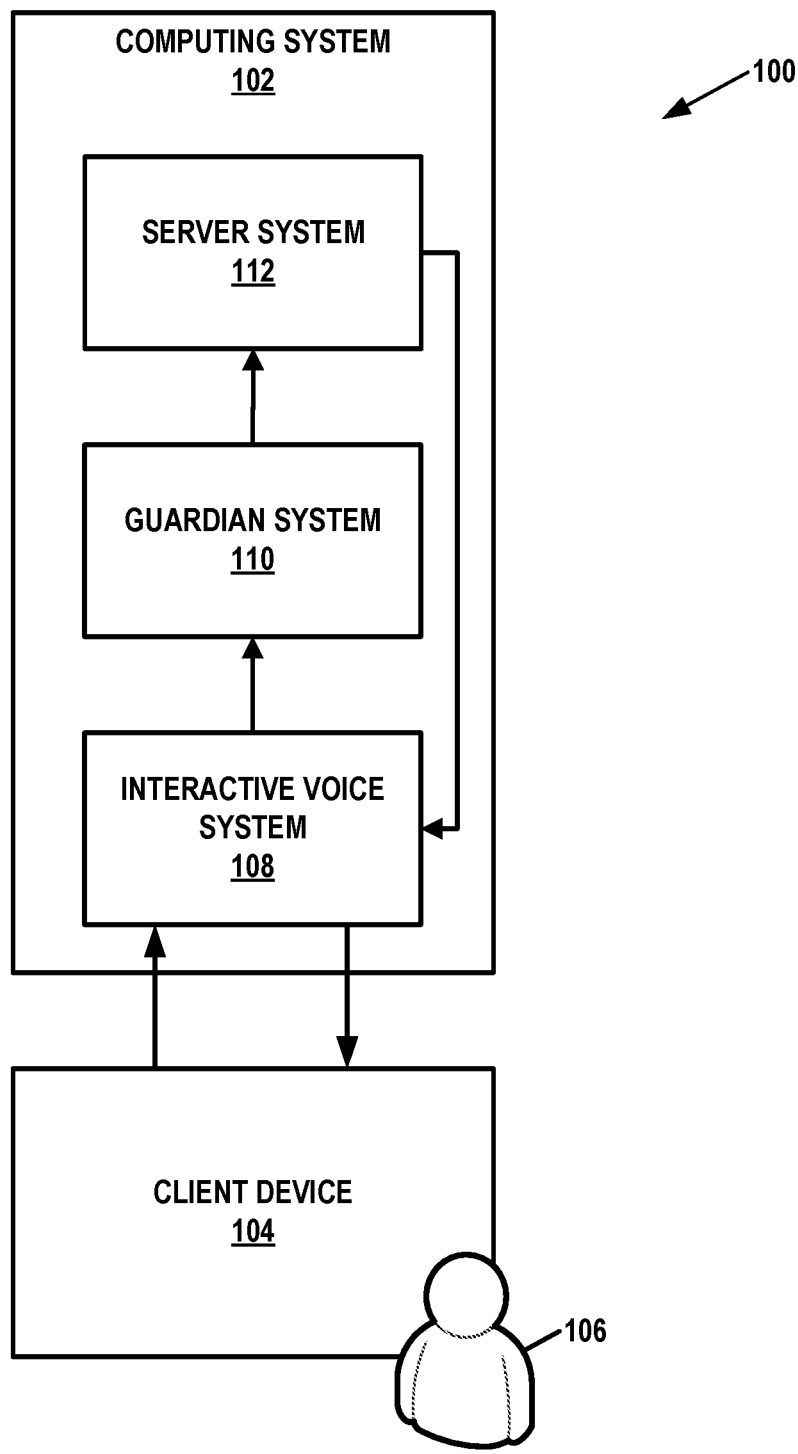
FIG. 2 is a block diagram illustrating an example system in which a guardian system acts as an output interceptor in accordance with one or more aspects of this disclosure.
Figure 3:
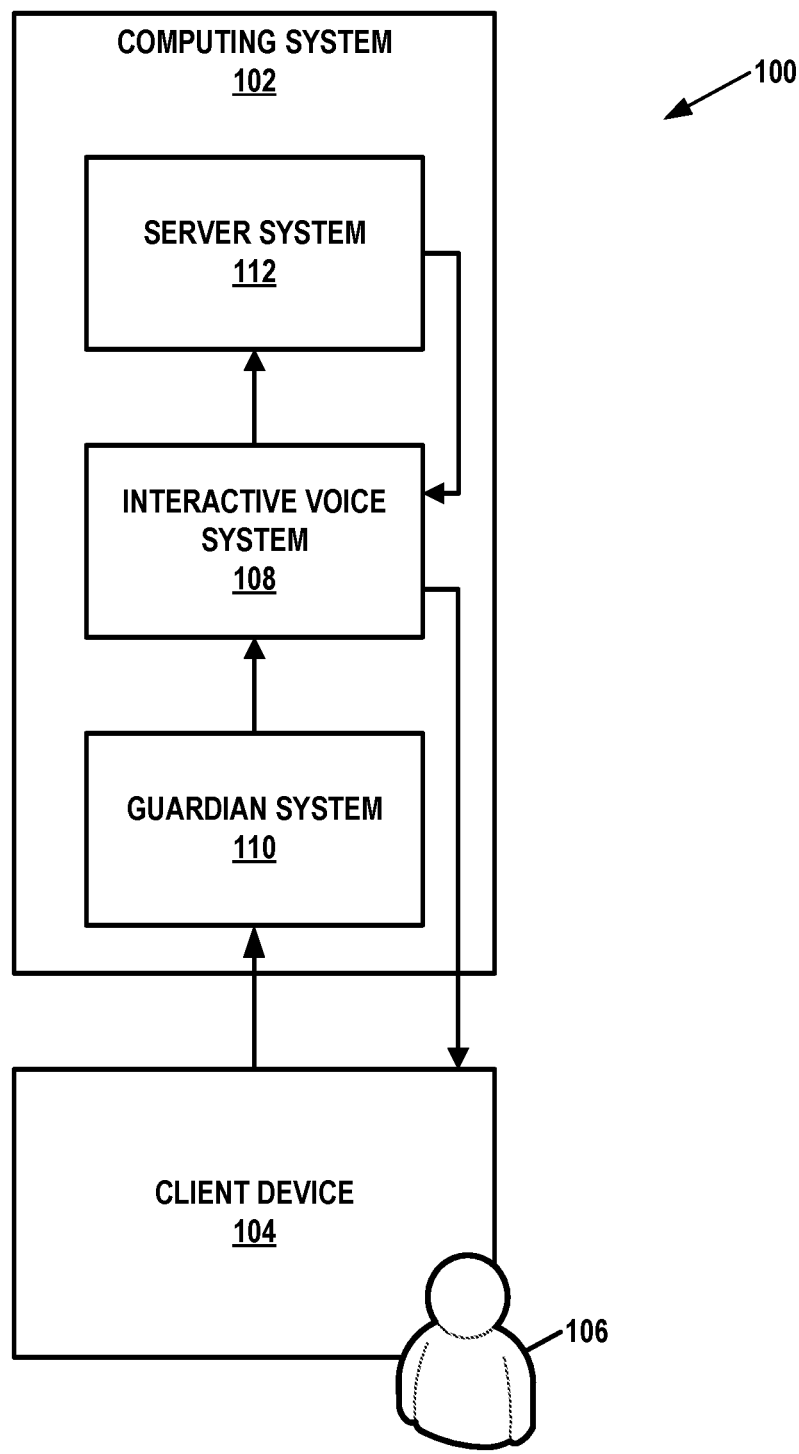
FIG. 3 is a block diagram illustrating an example system in which a guardian system acts as an input interceptor in accordance with one or more aspects of this disclosure.
Figure 4:
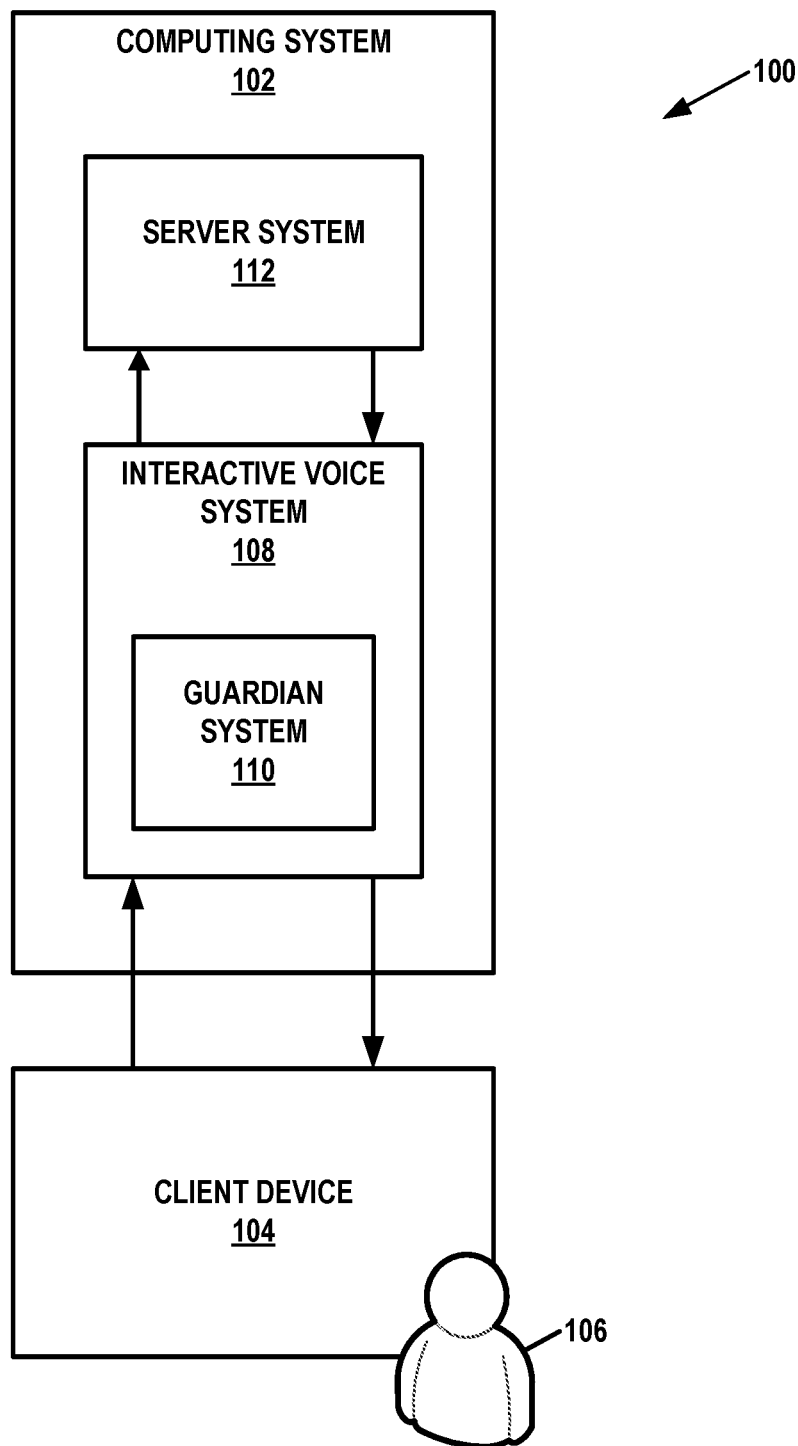
FIG. 4 is a block diagram illustrating an example system in which a guardian system is included in an interactive voice system in accordance with one or more aspects of this disclosure.

Guardian system 110 may be implemented in one of several ways with respect to IVS 108 and server system 112. For instance, FIG. 2 is a block diagram illustrating an example of system 100 in which guardian system 110 acts as an output interceptor in accordance with one or more aspects of this disclosure. FIG. 3 is a block diagram illustrating an example of system 100 in which guardian system 110 acts as an input interceptor in accordance with one or more aspects of this disclosure. FIG. 4 is a block diagram illustrating an example system in which guardian system 110 in included in IVS 108 in accordance with one or more aspects of this disclosure. In some examples, guardian system 110 may be implemented at least partially as one or more software applications running on client device 104, computing devices of computing system 102 that provide IVS 108, computing devices of computing system 102 that provide 112, and/or other computing devices. In some examples, guardian system 110 may be implemented at least partially in hardware client device 104, computing devices of computing system 102 that provide IVS 108, computing devices of computing system 102 that provide 112, and/or other computing devices.

In the example of FIG. 2, guardian system 110 may intercept output data generated by IVS 108 prior to the output data being obtained by server system 112. In the example of FIG. 2, server system 112 may receive non-sensitive information from IVS 108 and, in some examples, obfuscated sensitive information from guardian system 110. Server system 112 may generate data based on the data received by server system 112. IVS 108 may use the data generated by server system 112 to provide audio data to client device 104.

Thus, in an example in accordance with FIG. 2, guardian system 110 may obtain first audio data from IVS 108, where the first audio data represents one or more initial utterances. The one or more initial utterances may be utterances of user 106 or utterances rendered by client device 104 to user 106. Additionally, guardian system 110 may obtain second audio data from IVS 108, where the second audio data represent a subsequent utterance. In this example, guardian system 110 may generate, based on the first audio data, a prediction regarding whether a subsequent utterance of user 106 during the interactive voice session will contain sensitive information. Guardian system 110 may also determine, based on the prediction, whether to transmit the second audio data. In this example, based on a determination not to transmit the second audio data, guardian system 110 may replace, by the computing system, the second audio data with third audio data that is based on a voice of user 106. Guardian system 110 may transmit the third audio data to server system 112.

In the example of FIG. 3, guardian system 110 may intercept audio data from client device 104 before IVS 108 receives the audio data. Thus, in the example of FIG. 3, guardian system 110 may analyze the audio data from client device 104 to predict and obfuscate sensitive-information utterances. Guardian system 110 may forward audio data to IVS 108, including non-sensitive utterances and, in some examples, obfuscated sensitive-information utterances. IVS 108 may handle the received audio data as though guardian system 110 were not present. As in other examples, IVS 108 may generate output data, server system 112 may obtain the output data, server system 112 may process the output data, server system 112 may generate data based on the received output data, and IVS 108 may use the data generated by server system 112 to provide audio data to client device 104.

Thus, in the example of FIG. 3, guardian system 110 may obtain first audio data representing one or more initial utterances during an interactive voice session with IVS 108. Furthermore, in this example, guardian system 110 may generate, based on the first audio data, a prediction regarding whether a subsequent utterance of user 106 during the interactive voice session will contain sensitive information. Guardian system 110 may obtain second audio data representing the subsequent utterance. In this example, guardian system 110 may determine, based on the prediction, whether to transmit the second audio data. Based on a determination not to transmit the second audio data, guardian system 110 may replace the second audio data with third audio data that is based on a voice of user 106. In this example, guardian system 110 may transmit the first audio data and the third audio data to IVS 108 and not transmit the second audio data to IVS 108.

In the example of FIG. 4, guardian system 110 is included in IVS 108. In the example of FIG. 4, guardian system 110 may operate in a manner similar to FIG. 2 or FIG. 3, except that guardian system 110 is implemented as part of IVS 108 instead of being implemented as a separate system.

As briefly noted above, in accordance with one or more techniques of this disclosure, when guardian system 110 obfuscates a sensitive-information utterance, guardian system 110 may replace the sensitive-information utterance with replacement audio data that is based on the voice of user 106. In other words, the replacement audio data represents sound that sounds like the voice of user 106. The replacement audio data does not represent sound of sensitive information. For example, if the sensitive-information utterance is "321 Evergreen Street," the replacement audio data may represent the sound of "123 Fake Street." In some examples, guardian system 110 may generate the replacement audio data based on snippets of previously recorded sound of the voice of user 106. In some examples, guardian system 110 may extract vocal characteristics of the voice of user 106 and use the extracted vocal characteristics to synthesize the replacement audio data.

Replacing a sensitive-information utterance with replacement audio data that is based on the voice of user 106 may address several issues. For example, use of replacement audio data instead of an altered form of the original sensitive-information utterance may prevent an attacker from potentially recovering the sensitive-information utterance from the altered form of the sensitive-information utterance. In another example, IVS 108 may be configured to expect to receive audio data at the time of the sensitive-information utterance. If IVS 108 does not receive audio data, does not receive audio data containing speech sounds, or does not receive audio data containing speech sounds representing a particular type of data, IVS 108 might not be able to proceed to a next operation and/or may generate audio response data representing sounds to prompt user 106 to provide the information again. This may result in user 106 providing the sensitive information multiple times without IVS 108 being able to perform an expected operation, which may cause frustration and may make the sensitive information more likely to be improperly obtained. Using a replacement utterance in place of a sensitive-information utterance may help to avoid this problem, because IVS 108 may continue operation based on the replacement utterance.

Furthermore, use of replacement audio data that is based on the voice of user 106 may help with the operation of IVS 108. For instance, the audio data received by IVS 108 could contain the vocal sounds of multiple people, e.g., in the case where multiple people are in the same room as user 106. However, IVS 108 may need to distinguish between the vocal sounds of the multiple people to ensure that IVS 108 is acting upon audio data of the person involved in the interactive voice session with IVS 108. Accordingly, if the replacement audio data generated by guardian system 110 were not based on the voice of user 106, IVS 108 may assume that the replacement audio data represents the voice of another person, and may disregard the replacement audio data. Because IVS 108 may disregard the audio data in this scenario, IVS 108 may assume that user 106 has not provided a response and a similar problem to that described in the previous paragraph may occur (e.g., user 106 needing to repeatedly provide the information). However, in examples where guardian system 110 generates the replacement audio data based on the voice of user 106, IVS 108 may determine that user 106 has provided information and may continue operation. In this way, use of the replacement audio data may avoid user frustration, avoid user 106 providing the sensitive information multiple times, and may prevent IVS 108 and/or server system 112 from obtaining the sensitive information.

Hence, in accordance with some examples of this disclosure, guardian system 110 may obtain first audio data representing one or more initial utterances during an interactive voice session with IVS 108. Guardian system 110 may generate, based on the first audio data, a prediction regarding whether a subsequent utterance of user 106 during the interactive voice session will contain sensitive information. The subsequent utterance follows the one or more initial utterances in time. Guardian system 110 may subsequently obtain second audio data representing the subsequent utterance. Guardian system 110 may determine, based on the prediction, whether to transmit the second audio data. Based on a determination not to transmit the second audio data, guardian system 110 may replace the second audio data with third audio data that is based on a voice of user 106 and may transmit the third audio data. For instance, guardian system 110 may transmit the first audio data and the third audio data to IVS 108 and not transmit the second audio data to IVS 108. Alternatively, in some examples, guardian system 110 may obtain the first audio data from IVS 108, obtain the second audio data from IVS 108, and transmit the third audio data to server system 112.

In some examples, guardian system 110 is configured to determine whether to transmit sensitive-information utterances via IVS 108. As described in greater detail elsewhere in this disclosure, guardian system 110 may determine whether to transmit the sensitive-information utterances to IVS 108 based on a risk profile of IVS 108. For example, different users may use different IVS's. For instance, a first user may use the SIRI™ voice assistant system from Apple Inc., a second user may use ALEXA™ from Amazon.com Inc., a third user may use a special-purpose application that includes a voice interface, a fourth user may use an interactive voice system in a web application, and so on.

To accommodate a wide range of users, server system 112 may be able to act on data received via multiple interactive voice systems. However, different interactive voice systems may have different levels of security. For example, a first IVS may be configured to process voice data locally on client device 104 and only transmit encrypted data (e.g., encrypted semantic data) to server system 112. However, a second IVS may be configured to process voice data at a location separate from client device 104. In this example, the second IVS may or may not provide adequate measures to prevent disclosure of sensitive information, such as audio data of sensitive-information utterances or semantic content of sensitive-information utterances. Thus, in this example, it may be acceptable for sensitive information to be transmitted via the first IVS but not the second IVS. Moreover, the same IVS may treat different classes of sensitive information differently. Thus, it might be safe to transmit one class of sensitive information on an IVS but not safe to transmit another class of sensitive information on the same IVS.

Hence, in accordance with one or more techniques of this disclosure, guardian system 110 may obtain first audio data representing one or more initial utterances (e.g., of user 106, rendered by client device 104, etc.) during an interactive voice session with IVS 108. Additionally, guardian system 110 may generate, based on the first audio data, a prediction regarding whether a subsequent utterance of user 106 in the interactive voice session will contain sensitive information. The subsequent utterance follows the one or more initial utterances in time. Guardian system 110 may also obtain second audio data representing the subsequent utterance. Guardian system 110 may determine, based on the prediction and based on a risk profile of IVS 108, whether to transmit the second audio data to IVS 108. Based on the determination to transmit the second audio data to IVS 108, guardian system 110 may transmit the second audio data to IVS 108. Otherwise, guardian system 110 does not transmit the second audio data to IVS 108. In some examples, rather than not transmitting the second audio data, guardian system 110 may transmit replacement audio data to IVS 108, obfuscated audio data to IVS 108, or no audio data to IVS 108.

Although many examples of this disclosure are described with respect to audio data, some examples of this disclosure may use text data instead of audio data. Thus, in such examples, guardian system 110 may obtain first text data (e.g., text data generated by user 104, text data output by client device 104, etc.), generate, based on the first text data, a prediction regarding whether a subsequent text utterance of user 106 during an interactive text session will contain sensitive information. In this example, guardian system 110 may obtain second text data representing the subsequent text utterance and determine, based on the prediction, whether to transmit the second text data. In this example, based on a determination not to transmit the second text data, guardian system 110 may replace the second text data with third text data and transmit the third text data. In some examples, guardian system 110 may determine, based on the prediction and based on a risk profile of the interactive text system, whether to transmit the second text data to the interactive text system.

Figure 5:
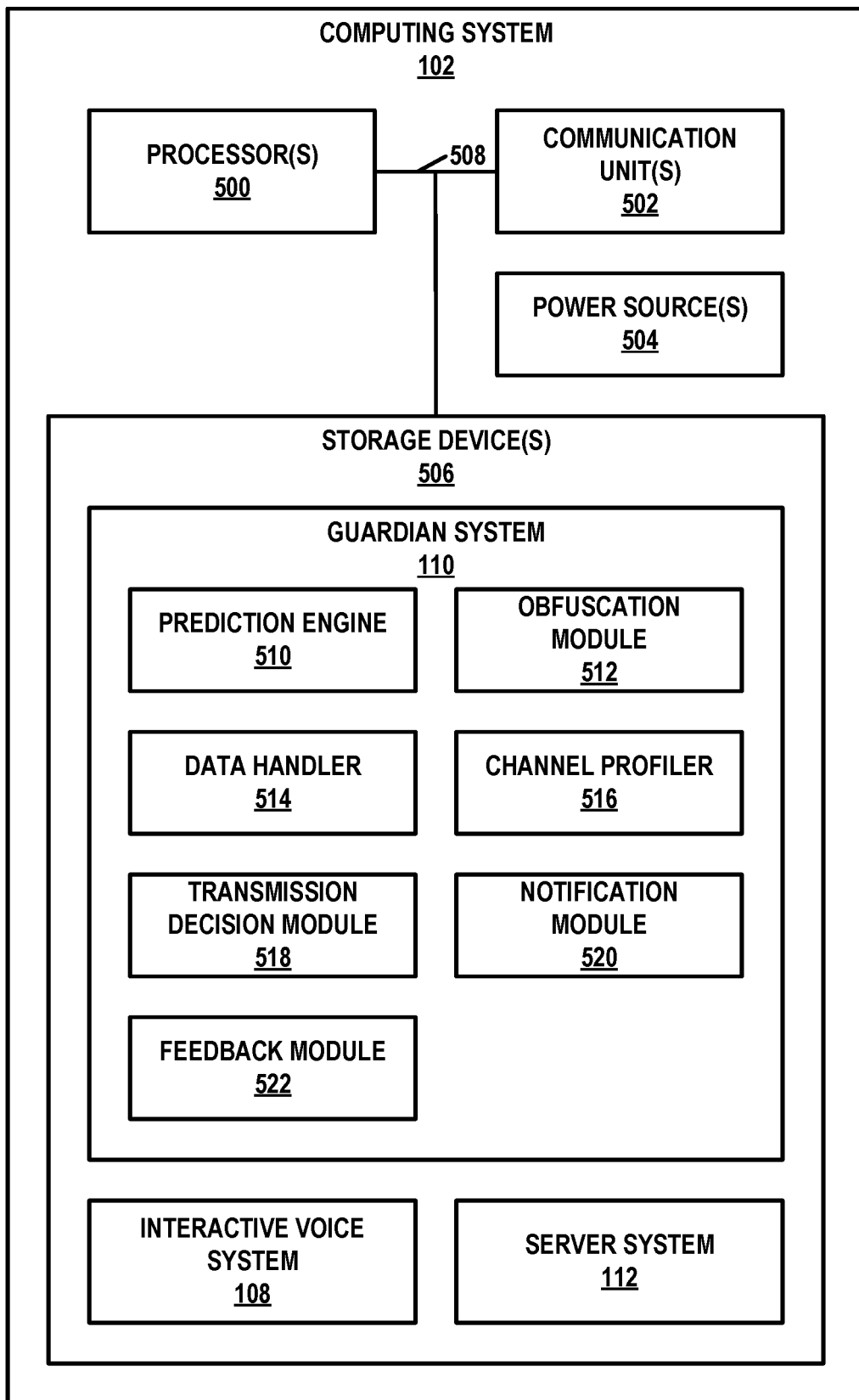
FIG. 5 is a block diagram illustrating example components of a computing system in accordance with one or more aspects of this disclosure.

FIG. 5 is a block diagram illustrating example components of computing system 102 in accordance with one or more aspects of this disclosure. FIG. 5 illustrates only one example of computing system 102, without limitation on many other example configurations of computing system 102.

As shown in the example of FIG. 5, computing system 102 includes one or more processors 500, one or more communication units 502, one or more power sources 504, one or more storage devices 506, and one or more communication channels 508. Computing system 102 may include other components. For example, computing system 102 may include input devices, output devices, display screens, and so on. Communication channel(s) 508 may interconnect each of components 500, 502, and 506 for inter-component communications (physically, communicatively, and/or operatively). In some examples, communication channel(s) 508 may include a system bus, a network connection, an inter-process communication data structure, or any other method for communicating data. Power source(s) 504 may provide electrical energy to components 500, 502, and 506. Storage device(s) 506 may store information required for use during operation of computing system 102.

Processor(s) 500 comprise circuitry configured to perform processing functions. For instance, one or more of processor(s) 500 may be a microprocessor, an application-specific integrated circuit (ASIC), a field-programmable gate array (FPGA), or another type of processing circuitry. In some examples, processor(s) 500 of computing system 102 may read and may execute instructions stored by storage device(s) 506. Processor(s) 500 may include fixed-function processors and/or programmable processors. Processor(s) 500 may be included in a single device or distributed among multiple devices.

Communication unit(s) 502 may enable computing system 102 to send data to and receive data from one or more other computing devices (e.g., via a communications network, such as a local area network or the Internet). In some examples, communication unit(s) 502 may include wireless transmitters and receivers that enable computing system 102 to communicate wirelessly with other computing devices. Examples of communication unit(s) 502 may include network interface cards, Ethernet cards, optical transceivers, radio frequency transceivers, or other types of devices that are able to send and receive information. Other examples of such communication units may include BLUETOOTH™, 3G, 4G, 5G, and WI-FI™ radios, Universal Serial Bus (USB) interfaces, etc. Computing system 102 may use communication unit(s) 502 to communicate with one or more other computing devices or systems, such as client device 104. Communication unit(s) 502 may be included in a single device or distributed among multiple devices.

Processor(s) 500 may read instructions from storage device(s) 506 and may execute instructions stored by storage device(s) 506. Execution of the instructions by processor(s) 500 may configure or cause computing system 102 to provide at least some of the functionality ascribed in this disclosure to computing system 102. Storage device(s) 506 may be included in a single device or distributed among multiple devices.

As shown in the example of FIG. 5, storage device(s) 506 may include computer-readable instructions associated with IVS 108, guardian system 110, and server system 112. Furthermore, in the example of FIG. 5, the computer-readable instructions associated with guardian system 110 may include computer-readable instructions associated with a prediction engine 510, an obfuscation module 512, a data handler 514, a channel profiler 516, a transmission decision module 518, a notification module 520, and a feedback module 522. In other examples, guardian system 110 may include more, fewer, or different components. For instance, in some examples, guardian system 110 does not include channel profiler 516, transmission decision module 518, notification module 520, and/or feedback module 522.

In general, prediction engine 510 takes utterances as input, processes the utterances in real-time to predict whether a next utterance contains sensitive information, and if so, predicts a duration of the sensitive-information utterance. Such utterances may be in the form of audio data. Obfuscation module 512 may obfuscate sensitive-information utterances. As described in detail elsewhere in this disclosure, obfuscation module 512 may obfuscate sensitive-information utterances in one or more of various ways. Data handler 514 handles outputs of prediction engine 510 and obfuscation module 512 to prepare an appropriate data buffer queued for further transmission. Channel profiler 516 may determine risk profiles of channels (e.g., interactive voice systems) for one or more types of sensitive information. The risk profile of a channel may indicate a level of trust in the channel, level of risk associated with transmitting data on the channel, or other information. Transmission decision module 518 may make determinations (e.g., real-time decisions) regarding whether to transmit an utterance over a communication channel. Transmission decision module 518 may make the determinations based on data from channel profiler 516. In response to a determination that an utterance is not safe to transmit on a channel, notification module 520 may generate a notification to user 106.

In some examples, storage device(s) 506 may be configured to at least temporarily store audio data. For instance, storage device(s) 506 may be configured to store audio data representing one or more initial utterances (e.g., initial utterances of user 104) during an interactive voice session with IVS 108, audio data representing subsequent utterances, and so on.

Figure 6:
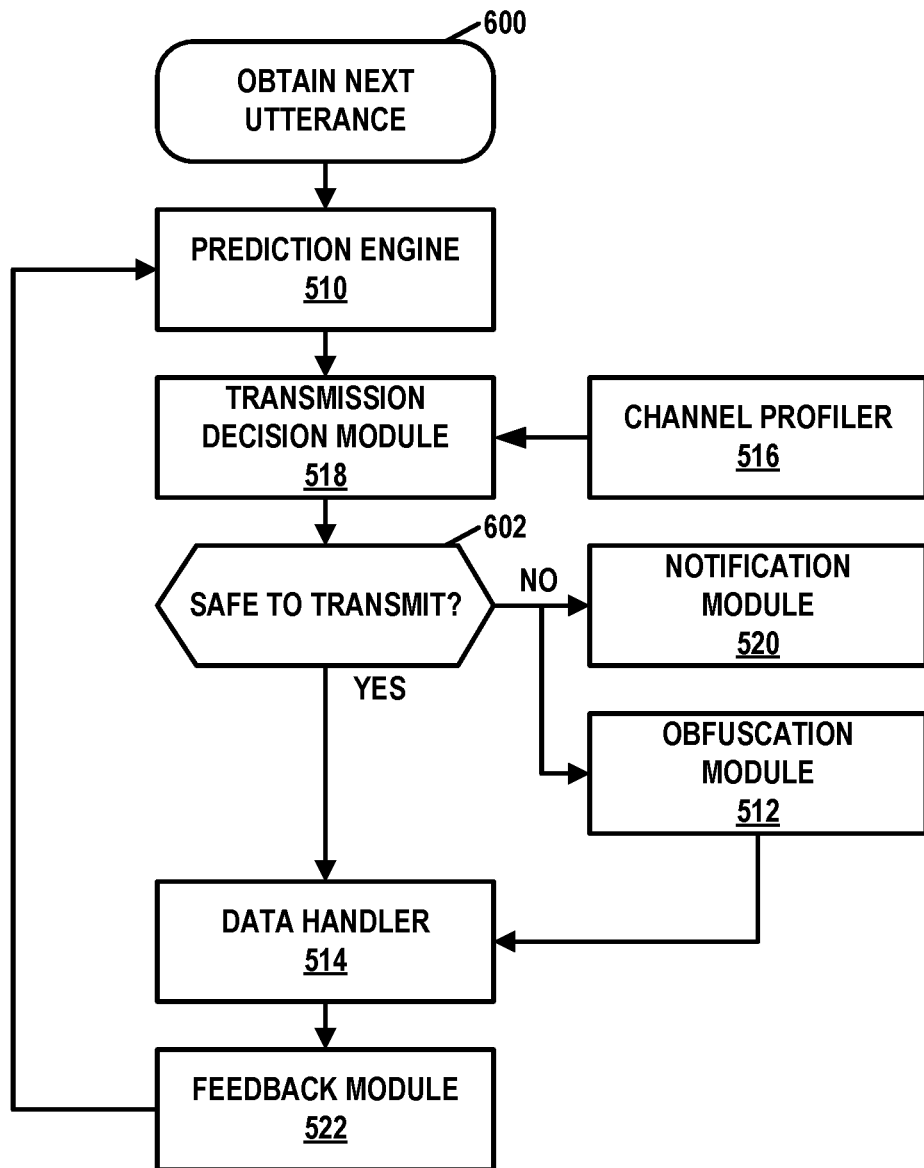
FIG. 6 is a flow diagram illustrating an example operation of a guardian system in accordance with one or more aspects of this disclosure.

FIG. 6 is a flow diagram illustrating an example operation of guardian system 110 in accordance with one or more aspects of this disclosure. The example of FIG. 6 is described with respect to the example of FIG. 5 but is not so limited.

In the example of FIG. 6, prediction engine 510 obtains an utterance (600). The utterance may correspond to sound within a first time window. Prediction engine 510 may determine whether a subsequent utterance (i.e., an utterance following the obtained utterance) is a sensitive-information utterance. The subsequent utterance may correspond to sound within a second time window that is advanced relative to the first time window. In some examples, the first and second time windows are overlapping. In some examples, the first and second time windows are non-overlapping. If the subsequent utterance is a sensitive-information utterance, prediction engine 510 may determine an expected temporal duration of the sensitive-information utterance.

Additionally, in the example of FIG. 6, transmission decision module 518 may determine based on a risk profile for a current channel whether it is safe to transmit the sensitive-information utterance via the current channel (602). For example, channel profiler 516 may determine, based on the risk profile for the current channel, a risk score for the current channel for a class of the sensitive information. Transmission decision module 518 may use the risk score for the current channel for the class of the sensitive information to determine whether to transmit the sensitive-information utterance via the current channel. The current channel is a channel through which guardian system 110 is currently configured to send data during an interactive voice session, receive the utterance during the interactive session, or into which guardian system 110 is incorporated. The risk profile for a channel comprises data regarding risks of transmitting sensitive information via the channel.

Based on a determination that it is safe to transmit the sensitive-information utterance on the current channel or based on a determination that the utterance is not a sensitive-information utterance ("YES" branch of 602), data handler 514 may transmit the sensitive-information utterance or non-sensitive utterance via the current channel, e.g., to IVS 108 or server system 112.

On the other hand, if transmission decision module 518 makes the determination that it is not safe to transmit the sensitive-information utterance ("NO" branch of 602), notification module 520 may generate a notification to user 106 that it may be unsafe to transmit the sensitive-information utterance via the current channel. For example, notification module 520 may generate an audio alert to be output by client device 104 or another device that notifies user 106 that it may be unsafe to transmit the sensitive-information utterance via the current channel. In some examples, notification module 520 may send an email message, text message, app-based notification, or other type of message to a device (e.g., phone, wearable device, etc.) associated with user 106 to notify user 106 that it may be unsafe to transmit the sensitive-information utterance via the current channel. In some examples, notification module 520 (or another unit of guardian system 110) may block the current channel. For instance, notification module 520 may configure guardian system 110 to prevent future use of the current channel for communication with server system 112.

Furthermore, if transmission decision module 518 makes the determination that it is not safe to transmit the sensitive-information utterance ("NO" branch of 602), obfuscation module 512 may obfuscate the sensitive-information utterance. Obfuscation module 512 may provide the obfuscated sensitive-information utterance to data handler 514. Data handler 514 may provide the obfuscated sensitive-information utterance to the current channel (e.g., IVS 108) or server system 112.

Obfuscation module 512 may obfuscate sensitive-information utterances in one or more ways. In some examples, obfuscation module 512 may replace a sensitive-information utterance with silence. In some examples, obfuscation module 512 may digitally add noise (e.g., white noise, Gaussian noise, pink noise, etc.) to the sensitive-information utterance to mask the sensitive-information utterance.

In some examples, obfuscation module 512 may obfuscate the sensitive-information utterance by digitally adding one or more blocking frequencies to the sensitive-information utterance. The one or more blocking frequencies may be or may include audible or inaudible frequencies. The one or more blocking frequencies may cancel out the frequencies of the sensitive-information utterance. In other examples, the one or more blocking frequencies do not cancel out the frequencies of the sensitive-information utterance. Rather, the one or more blocking frequencies may randomly distort or overshadow the frequencies of the sensitive-information utterance so that the sensitive-information utterance is not discernable by IVS 108.

In some examples, obfuscation module 512 may cause a speaker to physically generate the one or more blocking frequencies to obfuscate sensitive-information utterances. Thus, in the resulting combination the one or more blocking frequencies and the sensitive-information utterance, the sensitive-information utterance may have reduced audibility. The one or more blocking frequencies generated by the speaker may be or may include audible or inaudible frequencies. In examples where the one or more blocking frequencies are limited to inaudible frequencies, the sound of the one or more blocking frequencies may not disturb user 106. In some examples, the speaker is included in client device 104. In some examples, the speaker is included in another device, such as a device placed proximate to client device 104.

In the example of FIG. 6, feedback module 522 may provide feedback to prediction engine 510. Prediction engine 510 may use the feedback generated by feedback module 522 to improve the prediction of occurrences and/or temporal durations of sensitive-information utterances.

Figure 7:
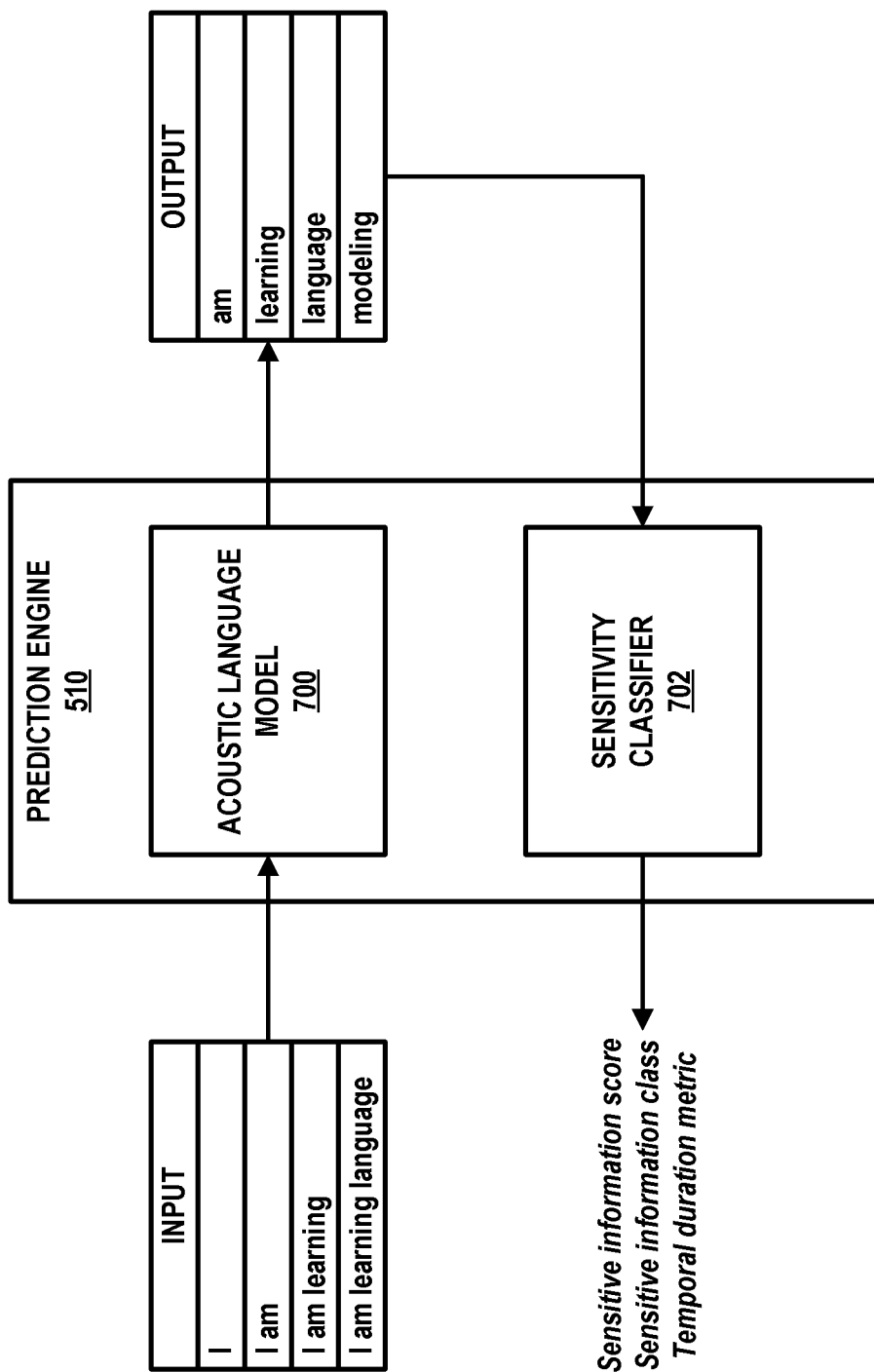
FIG. 7 is a block diagram illustrating an example prediction engine of a guardian system in accordance with one or more aspects of this disclosure.

FIG. 7 is a block diagram illustrating an example prediction engine 510 of guardian system 110 in accordance with one or more aspects of this disclosure. In the example of FIG. 7, prediction engine 510 includes an acoustic language model 700 and a sensitivity classifier 702.

Prediction engine 510 may obtain text based on utterances, such as utterances of user 106, utterances rendered by client device 104, etc. In some examples, guardian system 110 includes a speech-to-text engine that converts the utterances to text. In such examples, the speech-to-text engine may be implemented in accordance with any of the well-known speech-to-text engines or a custom speech-to-text engine. In other examples, IVS 108 generates the text based on the utterances and provides the text to guardian system 110.

Furthermore, prediction engine 510 may determine words of the text within a sliding window of consecutive words. The words within a window may be referred to as an n-gram, where n denotes the number of words that are in a group of consecutive words. Acoustic language model 700 may then determine a most probable word/phrase or type of word/phrase that follows an n-gram. For instance, if n is equal to 3, for a given window W with words $w_1$, $w_2$, and $w_3$, acoustic language model 700 may determine a probability of a next word $w_4$ as P ($w_4$|P($w_1$, $w_2$, $w_3$)). For example, for the group of words "I", acoustic language model 700 may determine that the most probable next word is "am"; for the group of words "I am", acoustic language model 700 may determine that the most probable next word is "learning"; for the group of words "I am learning", acoustic language model 700 may determine that the most probable next word is "language", and so on. In an example of determining a most probable type of word or phrase, acoustic language model 700 may determine that a next word is a series of numbers for the group of words "social security number is". Acoustic language model 700 may determine the most probable next word based on statistics regarding combinations of words.

Sensitivity classifier 702 may determine a confidence score that indicates a level of confidence that the subsequent utterance will contain sensitive information. For instance, sensitivity classifier 702 may determine based on statistics regarding a corpus of utterances a confidence score that indicates how likely it is that the subsequent utterance contains sensitive information given the utterances that came before the sensitive utterance. For example, the statistics may indicate that there is a sensitive information score (e.g., probability) of 0.98 that the next utterance contains sensitive information if the previous n-gram is "SSN is" or "Social Security Number is".

In some examples, sensitivity classifier 702 may determine a class of sensitive information potentially contained in a subsequent utterance. For example, classes of sensitive information may include social security numbers, bank account numbers, sets of symptoms, diseases, member identification numbers, etc. Sensitivity classifier 702 may determine that an utterance belongs to a class of sensitive information based on statistics regarding a corpus of utterances. For example, the statistics may indicate that there is a confidence score (e.g., probability) of 0.98 that the next utterance is a Social Security Number if the previous n-gram is "SSN is" or "Social Security Number is". In some examples, sensitivity classifier 702 may determine that the subsequent utterance will contain sensitive information in the class of sensitive information with a highest confidence score. In some examples, if the highest confidence score is below a predetermined threshold (e.g., 0.25, 0.5), prediction engine 510 may determine that the subsequent utterance will not contain sensitive information.

In some examples, the temporal duration metric may correspond to a length of time that it would take for user 106 to speak the next word/phrase. In some examples, the temporal duration metric may be the length of the next word/phrase in characters. In some examples, each sensitive information class has a corresponding temporal duration metric. The temporal duration metric for a sensitive information class indicates a typical length of time it takes to say a sensitive-information utterance belonging to the sensitive information class.

Sensitivity classifier 702 may determine the temporal duration metric based on statistics regarding lengths of time it takes to say a corresponding sensitive-information utterance. For example, sensitivity classifier 702 may obtain (e.g., from feedback module 522) information indicating how much time it takes user 106 (or a group of users) to speak the corresponding sensitive-information utterance. In this example, sensitivity classifier 702 may determine that the temporal duration metric based on these times. For instance, sensitivity classifier 702 may determine the temporal duration metric as an average of times, a median of times, a given percentage above the average/median of the times, and so on. Sensitivity classifier 702 may maintain different statistics (and therefore determine different temporal duration metrics) for different classes of sensitive information. In this way, prediction engine 510 may determine an expected temporal duration of an utterance.

As noted above, prediction engine 510 may use the feedback generated by feedback module 522 to improve the prediction of the occurrence and/or duration of sensitive-information utterances. For example, feedback module 522 may determine words in sounds generated by user 106 and update statistics regarding the probabilities of n-grams used by acoustic language model 700 based on the determined words. In some examples, feedback module 522 may determine temporal durations for uttering sensitive-information utterances. Prediction engine 510 may update a temporal duration metric based on the determined temporal durations for uttering sensitive-information utterances.

Figure 8:
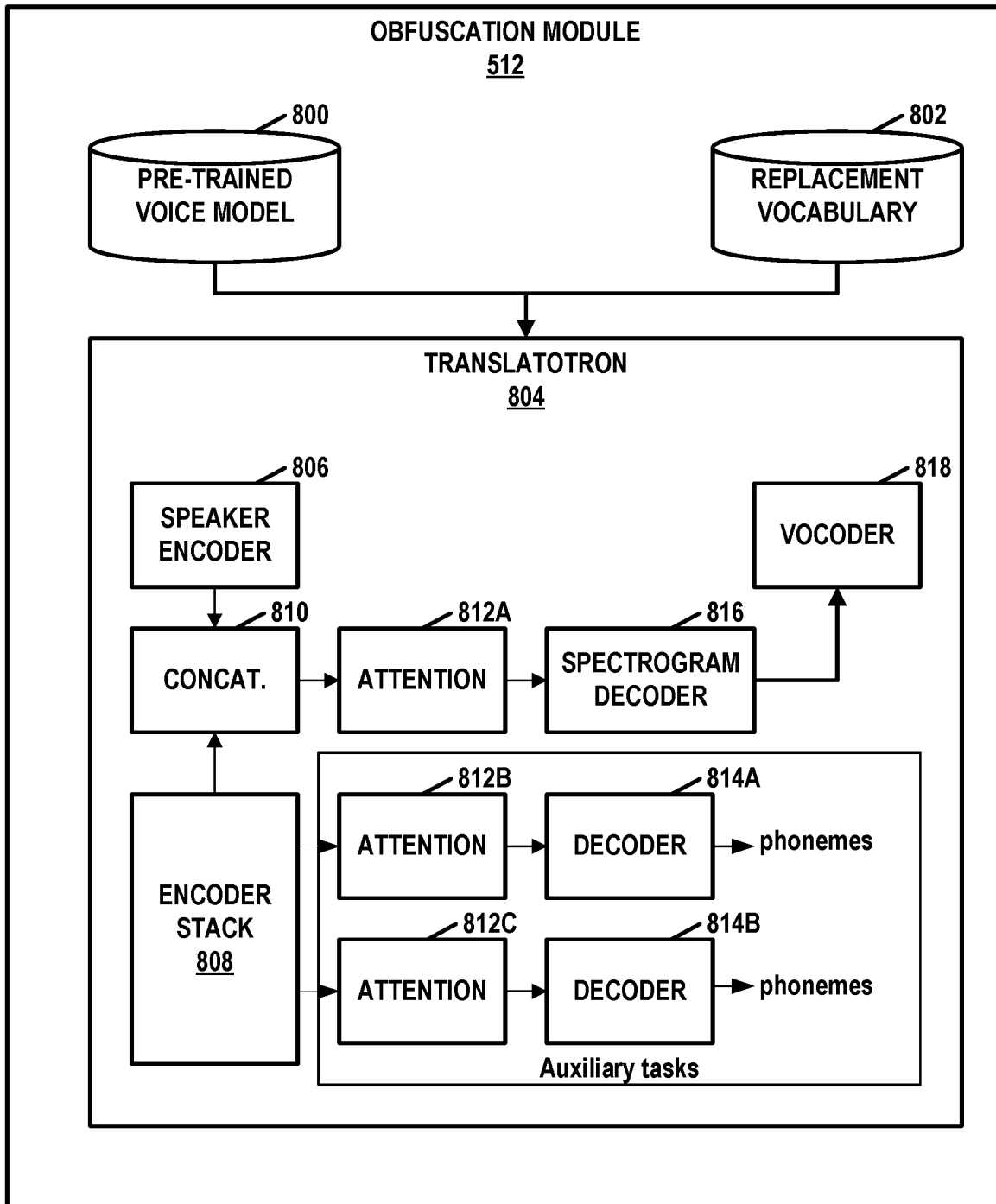
FIG. 8 is a block diagram illustrating an example obfuscation module of a guardian system in accordance with one or more aspects of this disclosure.

FIG. 8 is a block diagram illustrating an example obfuscation module 512 of guardian system 110 in accordance with one or more aspects of this disclosure. In the example of FIG. 8, obfuscation module 512 includes a pre-trained voice model 800, replacement vocabulary 802, and a translatotron 804. Pre-trained voice model 800 contains data for representing the acoustic qualities of the voice of user 106. Example acoustic qualities may include fundamental frequency, pitch, volume, timbre, tone, and so on. Replacement vocabulary 802 may include data indicating words that obfuscation module 512 may use as a replacement for a sensitive-information utterance.

In some examples, replacement vocabulary 802 may include one or more predetermined replacement utterances for each class of sensitive information of a plurality of classes of sensitive information. As described elsewhere in this disclosure, prediction engine 510 may determine a class of sensitive information for a subsequent utterance. For instance, prediction engine 510 may determine a confidence score for each of the classes of sensitive information and determine that the subsequent utterance will contain sensitive information belonging to the class of sensitive information having the greatest confidence score. Obfuscation module 512 may select one of the predetermined replacement utterances for the determined class of sensitive information as the replacement utterance for the subsequent utterance.

In the example of FIG. 8, translatotron 804 includes a speaker-encoder 806, an encoder stack 808, a concatenation unit 810, attention units 812A, 812B, 812C (collectively, "attention units 812"), decoder units 814A, 814B (collectively, "decoder units 814"), spectrogram decoder 816, and a vocoder 818.

Speaker-encoder 806 is a component that may condition spectrogram decoder 816 on a speaker's voice (e.g., the voice of user 106). In other words, speaker-encoder 806 may identify the speaker's voice characteristics, which spectrogram decoder 816 may later use to generate output that sounds similar to the original speaker. This may make the translated speech sound more natural and less jarring. In some examples, speaker-encoder 806 may apply a Fast Fourier transform (FFT) to digital audio samples of the voice of user 106 to generate spectrograms of the voice of user 106. The spectrograms generated by speaker-encoder 806 may form part of pre-trained model 800.

Encoder stack 808 may comprise a sequence-to-sequence encoder stack that takes a log-mel spectrogram as input and generates a vector of hidden states. The log-mel spectrogram corresponds to a time-step of an utterance (e.g., a sensitive-information utterance of user 106). A mel spectrogram is a spectrogram where the frequencies are converted to the 'mel scale'. In some examples, encoder stack 808 may map an 80-channel log-mel spectrogram into a vector of hidden states. The vector of hidden states may represent an encoded spectrogram for an obfuscated sensitive-information utterance. Encoder stack 808 may use replacement vocabulary 802 when generating the encoded spectrogram. For instance, internal layers of encoder stack 808 may generate values that map to words or phrases in replacement vocabulary 802. Subsequent layers of encoder stack 808 may then map the mapped words or phrases back to a vector of hidden states for the time-step corresponding to the input log-mel spectrogram.

Translatotron 804 may pass these hidden states through an attention-based alignment mechanism (i.e., attention units 812) to condition an autoregressive decoder (e.g., spectrogram decoder 816 or decoder 814A, 814B). Encoder stack 808 may be implemented as a stack of bidirectional LSTM layers (e.g., a stack of 8 bidirectional LSTM layers or another number of bidirectional LSTM layers). Concatenation unit 810 may concatenate the output of speaker-encoder 806 with the output of encoder stack 808. Attention is a type of input processing technique for neural networks. Attention enables neural networks (such as neural networks implemented in decoders 814 and spectrogram decoder 816) to focus on a subset of a complex input dataset or features. Attention mechanisms may be helpful in alignment of sequential data such as speech, text, etc.

Spectrogram decoder 816 may be an autoregressive decoder that takes, as input for each time-step, attention data, hidden states from encoder stack 808 (i.e., an encoded spectrogram) for the time-step, output of speaker-encoder 806, and output of spectrogram decoder 816 for a previous time-step. The output of spectrogram decoder 816 may refer to the output of spectrogram decoder 816 as a "target spectrogram." The target spectrogram represents sounds of an obfuscated sensitive-information utterance for the current time-step. Because spectrogram decoder 816 uses the output of speaker-encoder 816 as input, the obfuscated sensitive-information utterance may have vocal characteristics of user 106. In an example where encoder stack 808 maps an 80-channel log-mel spectrogram into a vector of hidden states, spectrogram decoder 816 may generate 1025-dimensional log spectrogram frames corresponding to generated speech. Spectrogram decoder 816 may be implemented with pre-net, autoregressive LSTM stack, and post-net components. Vocoder 818 transforms the target spectrogram to a time domain waveform that represents speech. Because the target spectrograms have vocal characteristics of user 106, the voice represented in the time-domain waveforms generated by vocoder 818 may sound like user 106.

Translatotron 804 may use decoders 814 to generate sequences of phonemes based on intermediate output of encoder stack 808. For instance, decoder 814A may generate a sequence of phonemes represented by a sensitive-information utterance. Decoder 814B may generate a sequence of phonemes in an obfuscated sensitive-information utterance. Loss values may be calculated based on the sequences of phonemes during training of encoder stack 808. The loss values may then be used for training encoder stack 808. Each of decoders 814 may be an LSTM decoder. For instance, decoders 814 may be 2-layer LSTMs with single-head additive attention. Decoders 814 and spectrogram decoder 816 may use attention dropout and LSTM zoneout regularization, e.g., with a probability of 0.1.

In some examples, rather than use translatotron 804, obfuscation module 512 may be configured with a plurality of voice profiles. Obfuscation module 512 may compare one or more characteristics of the voice of user 106 to characteristics of the voice profiles. Obfuscation module 512 may then select one of the voice profiles that most closely corresponds to the voice of user 106. Obfuscation module 512 may then apply a text-to-speech engine (such as any of the known text-to-speech engines known in the art) to convert utterances, including replacement utterances, into audio data using the selected voice profile. In this way, obfuscation module 512 may generate replacement audio data. Because the utterances, including replacement utterances, are generated using the text-to-speech engine, it may not be possible to determine that the resulting speech includes an obfuscated utterance.

Figure 9:
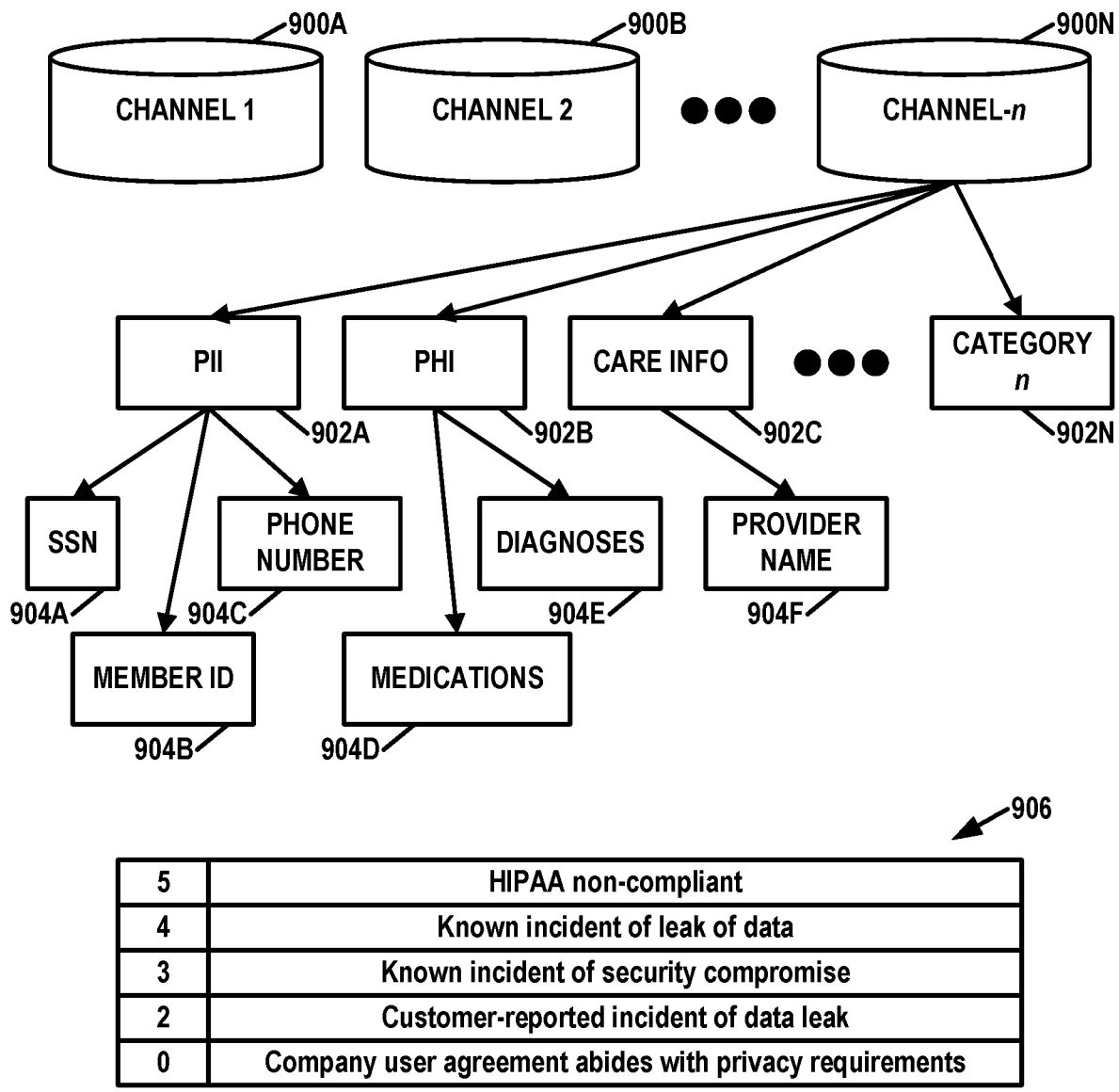
FIG. 9 is a conceptual diagram illustrating an example hierarchy of sensitive information for use by a channel profiler in accordance with one or more aspects of this disclosure.

FIG. 9 is a conceptual diagram illustrating an example hierarchy of sensitive information for use by channel profiler 516 in accordance with one or more aspects of this disclosure. In the example of FIG. 9, channel profiler 516 stores risk profiles 900A-900N (collectively, "risk profiles 900") for a plurality of channels. Each of risk profiles 900 corresponds to a different channel through which information can be conveyed from user 106 to server system 112. Example types of channels may include different types of voice assistant systems, different web applications, different native applications, and so on.

Each of risk profiles 900 may include data regarding categories 902A-902N (collectively, "categories 902"). Each of categories 902 represents a different type of sensitive information. For instance, category 902A represents personally identifiable information (PII), category 902B represents patient health information (PHI), category 902C represent care information, category 902N may represent another category of sensitive information.

In the example of FIG. 9, category 902A (PII) includes risk nodes 904A, 904B, and 904C. Category 902B (PHI) includes risk nodes 904D and 904E. Category 902C (care information) includes risk node 904F. Category 902N may include other risk nodes, which are not shown in the example of FIG. 9 for the purpose of clarity. Risk nodes 904A-904F may be referred to collectively as "risk nodes 904." Each of risk nodes 904 may correspond to a specific class of sensitive information. For instance, in the example of FIG. 9, risk nodes 904A through 904F correspond to a Social Security Number (SSN), a member identifier (where a member may be a health insurance policyholder), a phone number, a list of medications, a list of diagnoses, and a healthcare provider name, respectively.

Each of risk nodes 904 is associated with a risk score in a scoring system. FIG. 9 shows an example scoring system 906. In scoring system 906, higher risk scores are associated with higher risk. For example, scoring system 906 associates a risk node with a risk score of 5 when a channel (e.g., channel 900N in the example of FIG. 9) is regulatory (e.g., Health Insurance Portability and Accountability Act (HIPAA), Personal Information Protection and Electronic Documents Act (PIPEDA, etc.) non-compliant with respect to the information corresponding to the risk node. Scoring system 906 associates the risk node with a risk score of 4 when the channel is associated with a known incident of a leak of data corresponding to the risk node. Scoring system 906 associates the risk node with a risk score of 3 when the channel is associated with a known incident of a security compromise with respect to the data corresponding to the risk node. Scoring system 906 associates the risk node with a risk score of 2 when there is a customer-reported incident of a data leak of the data corresponding to the risk node on the channel. Scoring system 906 associates the risk node with a risk score of 0 when a company user agreement abides with privacy requirements with respect to the data corresponding to the risk node. In other examples, higher risk scores are associated with lower risk.

As discussed elsewhere in this disclosure, prediction engine 510 may determine that a subsequent utterance is a sensitive-information utterance and may determine a class of the sensitive-information utterance. Channel profiler 516 may determine, based on scoring system 906, the risk score for the risk node corresponding to the class of the sensitive-information utterance. If the risk score for the risk node is above (or in other examples, below) a threshold, transmission decision module 518 may determine that the sensitive-information utterance cannot be transmitted on the channel. For example, prediction engine 510 may determine that a sensitive-information utterance is a phone number. In this example, transmission decision module 518 may determine whether a risk score for risk node 904C (which corresponds to phone numbers) is above (or in other examples, below) a threshold. In this example, if the risk score for the risk node 904C is above (or in other examples, below) the threshold, transmission decision module 518 may make a determination not to transmit the sensitive-information utterance. Otherwise, transmission decision module 518 may make a determination to transmit the sensitive-information utterance.

There may be different thresholds for different risk nodes 904. For instance, with respect to scoring system 906, the threshold for risk node 904A (Social Security Number) may be 2, the threshold for risk node 904B (member identifier) may be 3, the threshold for risk node 904C (phone number) may be 4, and so on.

In some examples, transmission decision module 518 may determine whether to transmit the sensitive-information utterance based on risk scores for multiple risk nodes 904. For example, transmission decision module 518 may add the risk scores for risk nodes in a category (e.g., one of categories 902). In this example, if the sensitive-information utterance is in any class within the category and the risk score for any risk node (or at least a given number of risk nodes) within the category is above (or in other examples, below) a threshold, transmission decision module 518 may make a determination not to transmit the sensitive-information utterance. In some examples, if any risk node (or at least a given number of risk nodes) in any category has a risk score above (or in other examples, below) a threshold, transmission decision module 518 may make a determination not the transmit the sensitive-information utterance.

In some examples, there may be different scoring systems 906 for different risk nodes 904. For example, a scoring system for one of risk nodes 904 may have values ranging from 0 to 3 and a scoring system for another one of risk nodes 904 may have values ranging from 0 to 10. Accordingly, in such examples, transmission decision module 518 may normalize the risk scores for risk nodes.

In some examples, transmission decision module 518 may determine whether to transmit an utterance on a channel based on a risk score for the channel and based on a confidence score for the utterance. In this example, the risk score for the channel may be the highest risk score of any of risk nodes 904. The confidence score for the utterance may correspond to a level of confidence that the utterance is a sensitive-information utterance. Prediction engine 510 may generate the confidence score. In some examples, the confidence score is a value in a range of [0, 1]. In some examples, transmission decision module 518 determines a combined score based on the risk score for the channel and the confidence score for the utterance. For instance, in some examples, transmission decision module 518 may determine the combined score as the risk score for the channel multiplied by the confidence score for the utterance. Transmission decision module 518 may determine, based on a comparison of the combined score to a threshold, whether to transmit the utterance via the channel. For example, transmission decision module 518 may make a determination not to transmit the utterance via the channel based on the combined score being greater than the threshold.

In some examples, each of risk nodes 904 corresponds to a different class of sensitive information and prediction engine 510 may determine confidence scores for the utterance for each of the classes of sensitive information. For example, prediction engine 510 may determine a confidence score of 0.8 for the member identifier class (risk node 904B), a confidence score of 0.1 for the phone number class (risk node 904C), etc. Additionally, transmission decision module 518 may determine a separate risk score for the channel for each class of sensitive information. The risk scores for the channel for the classes of sensitive information may be normalized across the classes of sensitive information. In this example, transmission decision module 518 may determine separate combined scores for each class of sensitive information. For instance, for each class of sensitive information, transmission decision module 518 may determine a combined score for the class of sensitive information by multiplying the risk score for the channel for the class of sensitive information by the confidence score for the class of sensitive information. Furthermore, transmission decision module 518 may determine an overall combined score for the channel as a maximum of the combined scores for the classes of sensitive information. Transmission decision module 518 may determine, based on a comparison of the overall combined score for the channel to a threshold, whether to transmit the utterance via the channel. For example, transmission decision module 518 may make a determination not to transmit the utterance via the channel based on the overall combined score for the channel being greater than the threshold. In this way, the decision of whether to transmit an utterance may be based on a combination of the confidence that the utterance is a sensitive-information utterance and a risk of disclosure of the sensitive-information utterance on the channel.

As described elsewhere in this disclosure, notification module 520 may generate a notification to user 106 in response to a determination that an utterance is not safe to transmit on a channel. In some examples, there may be different notifications depending on the class of sensitive information, combined score for the channel, combined score for the channel for the class of sensitive information, and/or other factors. For example, notification module 520 may generate a warning tone or beep with a speed or intensity that is derived from the class of sensitive information, combined score for the channel, and/or the combined score for the channel for the class of sensitive information. In some examples, notification module 520 may change a tone of the assistant to indicate risk. In other words, notification module 520 may change vocal characteristics and/or word choice of the assistant based on the risk, e.g., to convey confidence, worry, uncertainty, or other emotional tone. In some examples, notification module 520 may generate a visual notification to user 106 in response to a determination that an utterance is not safe to transmit on a channel. For example, notification module 520 may change a color of a light (e.g., from green to amber to red) based on the class of sensitive information, combined score for the channel, or the combined score for the channel for the class of sensitive information. In some examples, if the channel is an application on a mobile device or a browser window, notification module 520 may modify a graphical user interface to indicate a risk that the utterance may not be safe to transmit on the channel (e.g., based on the class of sensitive information, combined score for the channel, and/or the combined score for the channel for the class of sensitive information). In some examples, notification module 520 may cause a vibration unit of a device (e.g., client device 104) to vibrate at a frequency that is based on the class of sensitive information, combined score for the channel, and/or the combined score for the channel for the class of sensitive information.

Figure 10:
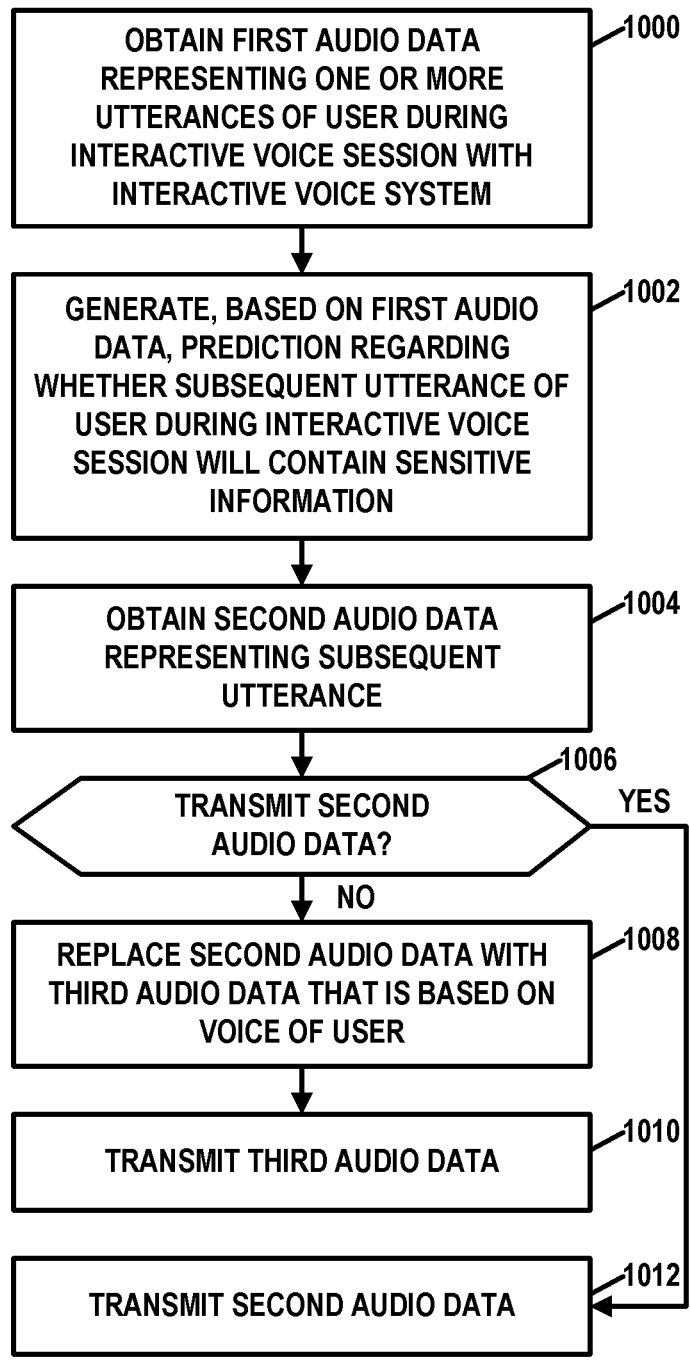
FIG. 10 is a flowchart illustrating an example method in accordance with one or more aspects of this disclosure.

FIG. 10 is a flowchart illustrating an example method in accordance with one or more aspects of this disclosure. Although the example of FIG. 10 is described with respect to the examples of FIG. 1 and FIG. 5, the method of FIG. 10 is not so limited.

In the example of FIG. 10, guardian system 110 may obtain first audio data representing one or more initial utterances during an interactive voice session with IVS 108 (1000). As discussed elsewhere in this disclosure, IVS 108 may a voice assistant system.

Additionally, prediction engine 510 of guardian system 110 may generate, based on the first audio data, a prediction regarding whether a subsequent utterance of user 106 during the interactive voice session will contain sensitive information, the subsequent utterance following the one or more initial utterances in time (1002). For example, the prediction may include a confidence score that indicates a level of confidence that the subsequent utterance will include a particular class of sensitive information Furthermore, guardian system 110 may obtain second audio data representing the subsequent utterance (1004). For instance, guardian system 110 may obtain the second audio data after generating the prediction regarding whether the subsequent utterance of user 106 will contain the sensitive information.

Guardian system 110 may determine, based on the prediction, whether to transmit the second audio data (1006). For instance, in some examples, as part of generating the prediction, prediction engine 510 may determine a confidence score that indicates a level of confidence that the subsequent utterance will contain the sensitive information. Prediction engine 510 may determine the confidence score as described above with respect to FIG. 7. In such examples, transmission decision module 518 may determine whether to transmit the second audio data based on a comparison of the confidence score and a threshold. For instance, transmission decision module 518 may make a determination to transmit the second audio data based on the confidence score being lower than the threshold. Transmission decision module 518 may make a determination not to transmit the second audio data based on the confidence score being greater than the threshold. In some examples, transmission decision module 518 may determine, based on the prediction and based on a risk profile of IVS 108, whether to transmit the second audio data to IVS 108.

Based on a determination not to transmit the second audio data ("NO" branch of 1006), guardian system 110 may replace the second audio data with third audio data that is based on a voice of user 106 (1008). Furthermore, prediction engine 510 may determine an expected temporal duration of the subsequent utterance. Prediction engine 510 may generate the third audio data based on the expected temporal duration of the subsequent utterance. In some examples, the third audio data represents an alternative, replacement utterance. In some examples, prediction engine 510 may synthesize the third audio data based on a predetermined replacement utterance and based on a spectrogram of the voice of user 106. Furthermore, obfuscation module 512 may determine, based on the first audio data, a class of the sensitive information. Obfuscation module 512 may generate the third audio data, where the third audio data represents an utterance containing replacement utterance in the same class of sensitive information. In some examples, obfuscation module 512 may generate a spectrogram of the voice of user 106 and generate the third audio data based on the spectrogram of the voice of user 106.

Additionally, guardian system 110 may transmit the third audio data (1010). For instance, in examples such as the example of FIG. 3, guardian system 110 may transmit the first audio data and the third audio data to IVS 108 and not transmit the second audio data to IVS 108. In other examples, such as the example of FIG. 2, guardian system 110 may obtain the first audio data from the IVS 108, obtain the second audio data from IVS 108, and transmit the third audio data to server system 112.

Otherwise, if guardian system 110 makes the determination to transmit the second audio data ("YES" branch of 1006), guardian system 110 may transmit the second audio data (1012). For instance, guardian system 110 may transmit the second audio data to IVS 108 or server system 112.

Figure 11:
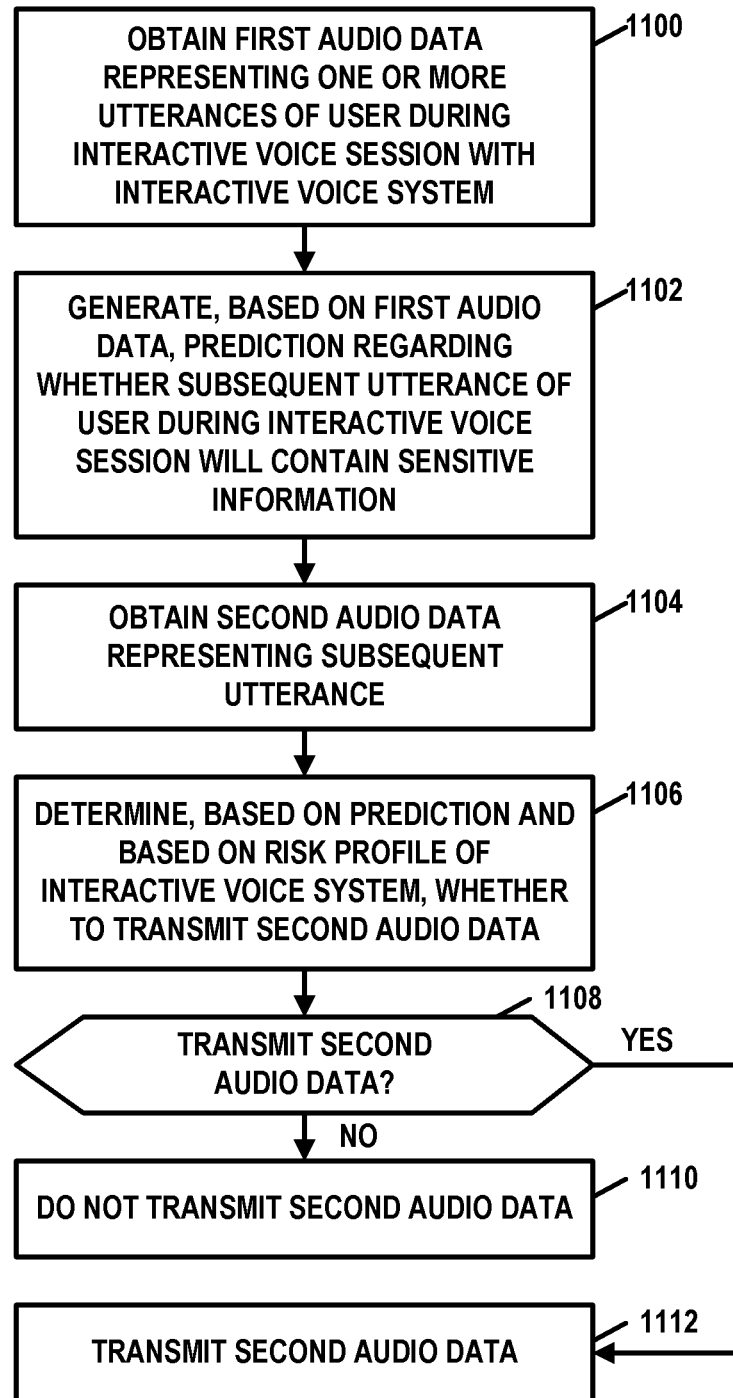
FIG. 11 is a flowchart illustrating an example method in accordance with one or more aspects of this disclosure.

FIG. 11 is a flowchart illustrating an example method in accordance with one or more aspects of this disclosure. Although the example of FIG. 11 is described with respect to the examples of FIG. 1 and FIG. 5, the method of FIG. 11 is not so limited.

In the example of FIG. 11, guardian system 110 obtains first audio data representing one or more initial utterances during an interactive voice session with interactive voice system 108 (1100). Although referred to as initial utterances for convenience, guardian system 110 may process utterances in the interactive voice session before these initial utterances.

Additionally, prediction engine 510 of guardian system 110 may generate, based on the first audio data, a prediction regarding whether a subsequent utterance of user 106 in the interactive voice session will contain sensitive information (1102). The subsequent utterance follows the one or more initial utterances in time.

Guardian system 110 may obtain second audio data representing the subsequent utterance (1104). For instance, guardian system 110 may obtain the second audio data from client device 104, from a microphone of client device 104, from a microphone of another device, or obtain the second audio data in another way.

Furthermore, guardian system 110 may determine, based on the prediction and based on a risk profile of IVS 108, whether to transmit the second audio data to the interactive voice system (1106). In some examples, the risk profile of IVS 108 includes a risk score for the interactive voice system for a class of sensitive information. In such examples, the prediction is a prediction regarding whether the subsequent utterance of user 106 in the interactive voice session will contain sensitive information in the class of sensitive information. As described above with respect to the example of FIG. 9, the risk score for IVS 108 for the class of sensitive information is based on at least one of: regulatory (e.g., HIPAA) compliance with respect to the class of sensitive information, a known leak of data in the class of sensitive information involving the interactive voice system, a known incident of a security compromise involving the interactive voice system with respect to the class of sensitive information, a customer-reported incident of a data leak involving the interactive voice system with respect to the class of sensitive information, or compliance of the interactive voice system with privacy requirements with respect to the class of sensitive information.

Furthermore, in some examples, the class of sensitive information is one of a plurality of classes of sensitive information. For each respective class of sensitive information in the plurality of classes of sensitive information, the risk profile of IVS 108 includes a respective risk score for IVS 108 for the respective class of sensitive information. For each respective class of sensitive information in the plurality of classes of sensitive information, prediction engine 510 may generate a respective confidence score for the respective class of sensitive information indicating a level of confidence that the subsequent utterance of user 106 in the interactive voice session will contain sensitive information in the class of sensitive information. In this example, as part of determining whether to transmit the second audio data to IVS 108, transmission decision module 518 may determine, for each respective class of sensitive information in the plurality of classes of sensitive information, based on the risk score for the interactive voice system for the respective class of sensitive information and the confidence score for the respective class of sensitive information, a combined score for the respective class of sensitive information. Transmission decision module 518 may determine, based on the combined scores for the classes of sensitive information, whether to transmit the second audio data. For instance, transmission decision module 518 may determine a maximum combined score among the combined scores for the classes of sensitive information and may determine whether to transmit the second audio data based on a comparison of the maximum combined score and a threshold.

Based on a determination not to transmit the second audio data to IVS 108 ("NO" branch of 1108), guardian system 110 does not transmit the second audio data to IVS 108 (1110). Based on a determination to transmit the second audio data to IVS 108 ("YES" branch of 1108), guardian system 110 may transmit the second audio data to the interactive voice system (1112).

The following is a non-limiting list of aspects that are in accordance with one or more techniques of this disclosure.

Aspect 1: A method includes obtaining, by a computing system, first audio data representing one or more initial utterances of a user during an interactive voice session with an interactive voice system; generating, by the computing system, based on the first audio data, a prediction regarding whether a subsequent utterance of the user during the interactive voice session will contain sensitive information, the subsequent utterance following the one or more initial utterances in time; obtaining, by the computing system, second audio data representing the subsequent utterance; determining, by the computing system, based on the prediction, whether to transmit the second audio data; and based on a determination not to transmit the second audio data: replacing, by the computing system, the second audio data with third audio data that is based on a voice of the user; and transmitting, by the computing system, the third audio data.

Aspect 2: The method of aspect 1, wherein the method further comprises transmitting, by the computing system, the first audio data and the third audio data to the interactive voice system and not transmitting the second audio data to the interactive voice system.

Aspect 3: The method of aspects 1 or 2, wherein: obtaining the first audio data comprises obtaining, by the computing system, the first audio data from the interactive voice system; obtaining the second audio data comprises obtaining, by the computing system, the second audio data from the interactive voice system; and transmitting the third audio data comprises transmitting, by the computing system, the third audio data to a server system.

Aspect 4: The method of any of aspects 1-3, wherein the interactive voice system is a voice assistant system.

Aspect 5: The method of any of aspects 1-4, wherein: generating the prediction comprises determining, by the computing system, a confidence score that indicates a level of confidence that the subsequent utterance will contain the sensitive information; and determining whether to transmit the second audio data comprises determining, by the computing system, whether to transmit the second audio data based on a comparison of the confidence score and a threshold.

Aspect 6: The method of any of aspects 1-5, wherein the method further comprises: determining, by the computing system, an expected temporal duration of the subsequent utterance; and generating, by the computing system, the third audio data based on the expected temporal duration of the subsequent utterance.

Aspect 7: The method of any of aspects 1-6, wherein: the third audio data represents an alternative utterance, the method further comprises: determining, by the computing system, based on the first audio data, a class of the sensitive information; and generating, by the computing system, the third audio data, wherein the third audio data represents an utterance containing a replacement utterance in the same class of sensitive information.

Aspect 8: The method of any of aspects 1-7, wherein: the method further comprises generating, by the computing system, a spectrogram of the voice of the user; and the method further comprises generating, by the computing system, the third audio data based on the spectrogram of the voice of the user.

Aspect 9: The method of any of aspects 1-8, wherein obtaining the second audio data comprises obtaining, by the computing system, the second audio data after generating the prediction regarding whether the subsequent utterance of the user will contain the sensitive information.

Aspect 10: A computing system includes one or more storage devices configured to store first audio data representing one or more initial utterances of a user during an interactive voice session with an interactive voice system; and processing circuitry configured to: generate, based on the first audio data, a prediction regarding whether a subsequent utterance of the user during the interactive voice session will contain sensitive information, the subsequent utterance following the one or more initial utterances in time; and obtain second audio data representing the subsequent utterance; determine, based on the prediction, whether to transmit the second audio data; and based on a determination not to transmit the second audio data: replace the second audio data with third audio data that is based on a voice of the user; and transmit the third audio data.

Aspect 11: The computing system of aspect 10, wherein the method further comprises transmitting, by the computing system, the first audio data and the third audio data to the interactive voice system and not transmitting the second audio data to the interactive voice system.

Aspect 12: The computing system of aspects 10 or 11, wherein: the processing circuitry is configured to obtain the first audio data from the interactive voice system; the processing circuitry is configured to obtain the second audio data from the interactive voice system; and the processing circuitry is configured to transmit the third audio data to a server system.

Aspect 13: The computing system of any of aspects 10-12, wherein the interactive voice system is a voice assistant system.

Aspect 14: The computing system of any of aspects 10-13, wherein: the processing circuitry is configured such that, as part of generating the prediction, the processing circuitry determines a confidence score that indicates a level of confidence that the subsequent utterance will contain the sensitive information; and the processing circuitry is configured such that, as part of determining whether to transmit the second audio data, the processing circuitry determines whether to transmit the second audio data based on a comparison of the confidence score and a threshold.

Aspect 15: The computing system of any of aspects 10-14, wherein the processing circuitry is further configured to: determine an expected temporal duration of the subsequent utterance; and generate the third audio data based on the expected temporal duration of the subsequent utterance.

Aspect 16: The computing system of any of aspects 10-15, wherein: the third audio data represents an alternative utterance, the processing circuitry is further configured to: determine, based on the first audio data, a class of the sensitive information; and generate the third audio data, wherein the third audio data represents an utterance containing a replacement utterance in the same class of sensitive information.

Aspect 17: The computing system of any of aspects 10-16, wherein: the processing circuitry is further configured to generate a spectrogram of the voice of the user; and the processing circuitry is further configured to generate the third audio data based on the spectrogram of the voice of the user.

Aspect 18: The computing system of any of aspects 10-17, wherein the processing circuitry is configured such that, as part of obtaining the second audio data, the processing circuitry obtains the second audio data after generating the prediction regarding whether the subsequent utterance of the user will contain the sensitive information.

Aspect 19: A computer-readable storage medium comprising instructions that, when executed, cause processing circuitry of a computing system to: obtain first audio data representing one or more initial utterances of a user during an interactive voice session with an interactive voice system; generate, based on the first audio data, a prediction regarding whether a subsequent utterance of the user during the interactive voice session will contain sensitive information, the subsequent utterance following the one or more initial utterances in time; and obtain second audio data representing the subsequent utterance; determine, based on the prediction, whether to transmit the second audio data; and based on a determination not to transmit the second audio data: replace the second audio data with third audio data that is based on a voice of the user; and transmit the third audio data.

For processes, apparatuses, and other examples or illustrations described herein, including in any flowcharts or flow diagrams, certain operations, acts, steps, or events included in any of the techniques described herein can be performed in a different sequence, may be added, merged, or left out altogether (e.g., not all described acts or events are necessary for the practice of the techniques). Moreover, in certain examples, operations, acts, steps, or events may be performed concurrently, e.g., through multi-threaded processing, interrupt processing, or multiple processors, rather than sequentially. Further certain operations, acts, steps, or events may be performed automatically even if not specifically identified as being performed automatically. Also, certain operations, acts, steps, or events described as being performed automatically may be alternatively not performed automatically, but rather, such operations, acts, steps, or events may be, in some examples, performed in response to input or another event.

Further, certain operations, techniques, features, and/or functions may be described herein as being performed by specific components, devices, and/or modules. In other examples, such operations, techniques, features, and/or functions may be performed by different components, devices, or modules. Accordingly, some operations, techniques, features, and/or functions that may be described herein as being attributed to one or more components, devices, or modules may, in other examples, be attributed to other components, devices, and/or modules, even if not specifically described herein in such a manner.

In one or more examples, the functions described may be implemented in hardware, software, firmware, or any combination thereof. If implemented in software, the functions may be stored on or transmitted over a computer-readable medium as one or more instructions or code and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers, processing circuitry, or one or more processors to retrieve instructions, code and/or data structures for implementation of the techniques described in this disclosure. A computer program product may include a computer-readable medium.

By way of example, and not limitation, such computer-readable storage media can include RAM, ROM, EEPROM, CD-ROM, or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), and Blu-ray disc, where disks usually reproduce data magnetically, while discs reproduce data optically with lasers. Combinations of the above should also be included within the scope of computer-readable media.

Instructions may be executed by processing circuitry (e.g., one or more processors, such as one or more DSPs, general purpose microprocessors, ASICs, FPGAs, or other equivalent integrated or discrete logic circuitry), as well as any combination of such components. Accordingly, the term "processor" or "processing circuitry" as used herein, may refer to any of the foregoing structures or any other structure suitable for implementation of the techniques described herein. In addition, in some aspects, the functionality described herein may be provided within dedicated hardware and/or software modules. Also, the techniques could be fully implemented in one or more circuits or logic elements.

The techniques of this disclosure may be implemented in a wide variety of devices or apparatuses, including a wireless communication device or wireless handset, a microprocessor, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

What is claimed is:

1. A method comprising:
   obtaining, by a computing system, first audio data representing one or more initial utterances of a user during an interactive voice session with an interactive voice system;
   for each class of sensitive information in a plurality of classes of sensitive information, determining, by the computing system, based on the first audio data, a confidence score for the class of sensitive information, wherein the confidence score for the class of sensitive information indicates a level of confidence that a subsequent utterance of the user during the interactive voice session will belong to the class of sensitive information, the subsequent utterance of the user following the one or more initial utterances in time;
   determining, by the computing system, a risk profile for a communication channel through which the first audio data is to be transmitted, wherein the risk profile for the communication channel includes a plurality of risk scores associated with transmitting the plurality of classes of sensitive information over the communication channel, respectively;
   determining, by the computing system, that a specific class of sensitive information has the highest confidence score among the plurality of classes of sensitive information, wherein a specific risk score of the plurality of risk scores in the determined risk profile is associated with transmitting the specific class of sensitive information over the communication channel;
   obtaining, by the computing system, second audio data representing the subsequent utterance of the user;
   determining, by the computing system, based on a first comparison of the highest confidence score with a first predetermined threshold and a second comparison of the specific risk score with a second predetermined threshold, whether to prevent transmission of the second audio data; and
   based on determining to prevent transmission of the second audio data:
      generating, by the computing system, third audio data, wherein the third audio data represents a replacement utterance in the specific class of sensitive information, and the third audio is based on a voice of the user;
      replacing, by the computing system, the second audio data with the third audio data; and
      transmitting, by the computing system, the third audio data.

2. The method of claim 1, wherein the method further comprises transmitting, by the computing system, the first audio data and the third audio data to the interactive voice system and not transmitting the second audio data to the interactive voice system.

3. The method of claim 1, wherein:
   obtaining the first audio data comprises obtaining, by the computing system, the first audio data from the interactive voice system;
   obtaining the second audio data comprises obtaining, by the computing system, the second audio data from the interactive voice system; and
   transmitting the third audio data comprises transmitting, by the computing system, the third audio data to a server system.

4. The method of claim 1, wherein the interactive voice system is a voice assistant system.

5. The method of claim 1, wherein the method further comprises:
   determining, by the computing system, an expected temporal duration of the subsequent utterance; and
   generating, by the computing system, the third audio data based on the expected temporal duration of the subsequent utterance.

6. The method of claim 1, wherein:
   the method further comprises generating, by the computing system, a spectrogram of the voice of the user; and
   generating the third audio data comprises generating, by the computing system, the third audio data based on the spectrogram of the voice of the user.

7. The method of claim 1, wherein obtaining the second audio data comprises obtaining, by the computing system, the second audio data after generating a prediction regarding whether the subsequent utterance of the user will contain the sensitive information.

8. A computing system comprising:
   one or more storage devices configured to store first audio data representing one or more initial utterances of a user during an interactive voice session with an interactive voice system; and processing circuitry configured to:
for each class of sensitive information in a plurality of classes of sensitive information, determine, based on the first audio data, a confidence score for the class of sensitive information, wherein the confidence score for the class of sensitive information indicates a level of confidence that a subsequent utterance of the user during the interactive voice session will belong to the class of sensitive information, the subsequent utterance of the user following the one or more initial utterances in time;
determine a risk profile for a communication channel through which the first audio data is to be transmitted, wherein the risk profile for the communication channel includes a plurality of risk scores associated with transmitting the plurality of classes of sensitive information over the communication channel, respectively;
determine that a specific class of sensitive information has the highest confidence score among the plurality of classes of sensitive information, wherein a specific risk score of the plurality of risk scores in the determined risk profile is associated with transmitting the specific class of sensitive information over the communication channel;
obtain second audio data representing the subsequent utterance of the user;
determine, based on a first comparison of the highest confidence score with a first predetermined threshold and a second comparison of the specific risk score and a second predetermined threshold, whether to prevent transmission of the second audio data; and
based on determining to prevent transmission of the second audio data:
generate third audio data, wherein the third audio data represents a replacement utterance in the specific class of sensitive information and the third audio is based on a voice of the user;
replace the second audio data with the third audio data; and
transmit the third audio data.

9. The computing system of claim 8, wherein the method further comprises transmitting, by the computing system, the first audio data and the third audio data to the interactive voice system and not transmitting the second audio data to the interactive voice system.

10. The computing system of claim 8, wherein:
the processing circuitry is configured to obtain the first audio data from the interactive voice system;
the processing circuitry is configured to obtain the second audio data from the interactive voice system; and
the processing circuitry is configured to transmit the third audio data to a server system.

11. The computing system of claim 8, wherein the interactive voice system is a voice assistant system.

12. The computing system of claim 8, wherein the processing circuitry is further configured to:
determine an expected temporal duration of the subsequent utterance; and
generate the third audio data based on the expected temporal duration of the subsequent utterance.

13. The computing system of claim 8, wherein:
the processing circuitry is further configured to generate a spectrogram of the voice of the user; and
the processing circuitry is configured to generate the third audio data based on the spectrogram of the voice of the user.

14. The computing system of claim 8, wherein the processing circuitry is configured such that, as part of obtaining the second audio data, the processing circuitry obtains the second audio data after generating a prediction regarding whether the subsequent utterance of the user will contain the sensitive information.

15. A non-transitory computer-readable storage medium comprising instructions that, when executed, cause processing circuitry of a computing system to:
obtain first audio data representing one or more initial utterances of a user during an interactive voice session with an interactive voice system;
for each class of sensitive information in a plurality of classes of sensitive information, determine, based on the first audio data, a confidence score for the class of sensitive information, wherein the confidence score for the class of sensitive information indicates a level of confidence that a subsequent utterance of the user during the interactive voice session will belong to the class of sensitive information, the subsequent utterance of the user following the one or more initial utterances in time;
determine a risk profile for a communication channel through which the first audio data is to be transmitted, wherein the risk profile for the communication channel includes a plurality of risk scores associated with transmitting the plurality of classes of sensitive information over the communication channel, respectively;
determine that a specific class of sensitive information has the highest confidence score among the plurality of classes of sensitive information, wherein a specific risk score of the plurality of risk scores in the determined risk profile is associated with transmitting the specific class of sensitive information over the communication channel;
obtain second audio data representing the subsequent utterance of the user;
determine, based on a first comparison of the highest confidence score with a first predetermined threshold and on a second comparison of the specific risk score and a second predetermined threshold, whether to prevent transmission of the second audio data; and
based on determining to prevent transmission of the second audio data:
generate third audio data, wherein the third audio data represents a replacement utterance in the specific class of sensitive information and the third audio is based on a voice of the user;
replace the second audio data with third audio data; and
transmit the third audio data.

* * * * *